(12) United States Patent
Narkunan et al.

(10) Patent No.: US 7,687,497 B2
(45) Date of Patent: Mar. 30, 2010

(54) C10-SUBSTITUTED CAMPTOTHECIN ANALOGS

(75) Inventors: Kesavaram Narkunan, San Antonio, TX (US); Xinghai Chen, San Antonio, TX (US); Harry Kochat, San Antonio, TX (US); Frederick Hausheer, Boerne, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 0 days.

(21) Appl. No.: 11/974,756

(22) Filed: Oct. 16, 2007

(65) Prior Publication Data
US 2009/0099166 A1 Apr. 16, 2009

(51) Int. Cl.
*A61K 31/4375* (2006.01)
*A61K 31/5377* (2006.01)
*A61P 35/00* (2006.01)
*C07F 7/10* (2006.01)

(52) U.S. Cl. ............... 514/233.2; 514/283; 544/69; 546/14

(58) Field of Classification Search ............ None
See application file for complete search history.

(56) References Cited

U.S. PATENT DOCUMENTS

| 5,726,181 | A | 3/1998 | Hausheer et al. |
| 5,910,491 | A | 6/1999 | Hausheer et al. |
| 6,136,978 | A * | 10/2000 | Curran et al. ............... 546/14 |
| 6,194,579 | B1 | 2/2001 | Hausheer |

OTHER PUBLICATIONS

U.S. Appl. No. 10/627,444.

* cited by examiner

*Primary Examiner*—Brandon J Fetterolf
*Assistant Examiner*—Anna Pagonakis
(74) *Attorney, Agent, or Firm*—Scott A. Whitaker

(57) ABSTRACT

The novel C10-modified camptothecin analogs, and pharmaceutically-acceptable salts thereof, of the present invention: (i) possess potent antitumor activity (i.e., in nanomolar or subnanomolar concentrations) for inhibiting the growth of human and animal tumor cells in vitro; (ii) are potent inhibition of Topoisomerase I; (iii) lack of susceptibility to MDR/MRP drug resistance; (iv) require no metabolic drug activation: (v) lack glucuronidation of the A-ring or B-ring; (vi) reduce drug-binding affinity to plasma proteins; (vii) maintain lactone stability; (viii) maintain drug potency; and (ix) possess a low molecular weight (e.g., MW<600).

4 Claims, No Drawings

C10-SUBSTITUTED CAMPTOTHECIN ANALOGS

FIELD OF THE INVENTION

The present invention relates to novel camptothecin analogs. More specifically, the present invention relates to camptothecin analogs, and pharmaceutically-acceptable salts thereof, wherein various types of covalent linkages will connect the novel side chain at the C10 position on the A-ring of said camptothecin analog (e.g., Karenitecin®).

BACKGROUND OF THE INVENTION

I. Camptothecin (CPT)

Camptothecin (CPT; IUPAC Nomenclature: (S)-4-Ethyl-4-hydroxy-1H-pyrano[3',4':6,7]indolizino[1,2-b]quinoline-3,14(4H,12H)-dione) and certain of its analogs have been shown to possess varying degrees of anti-neoplastic activity. Presently, two CPT analogs (Irinotecan™ and Topotecan™, as discussed below) have been approved for therapeutic use in the United States by the Food and Drug Administration (FDA) for various forms of solid neoplasms.

CPT was initially isolated in 1966 by Wall, et al., from *Camptotheca accuminata*, (Nyssaceae family) a Chinese yew. See, Wall, M. E., et al., Plant chemotherapeutic agents. I. The Isolation and Structure of Camptothecin, a Novel Alkaloidal Leukemia and Tumor Inhibitor from *Camptotheca Acuminata*. *J. Am. Chem. Soc.* 88:3888-3890 (1966)).

The structure of this originally isolated camptothecin (CPT) is shown below:

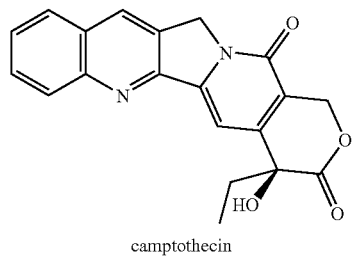

camptothecin

The pentacyclic ring system includes a pyztolo[3,4-b] quinoline (rings A, B and C), a conjugated pyridone ring D), and six membered lactone (ring E) with an 20-hydroxyl group. By the early 1970's, CPT had reached Phase I and Phase II clinical trials and although it was found to possess anti-tumor activity, there were numerous deleterious physiological side-effects associated with its use. The side-effects included, but were not limited to, severe and unpredictable myelosuppression, gastrointestinal toxicity, hemorrhagic cystitis, alopecia, diarrhea, nausea, vomiting and the like. These toxicities, found during early clinical studies, rendered the drug "unmanageable" during this time period. See, Muggia, F. M.; et al., Phase I Clinical Trial of Weekly and Daily Treatment With Camptothecin (NSC-100880): Correlation With Preclinical Studies. *Cancer Chemother. Rep.* 56:515-521 (1972); Schaeppi, U., et al., Toxicity of Camptothecin (NSC-100880). *Cancer Chemother. Rep.* 5:25-36 (1974).

In order to demonstrate both the utility and novelty of the present invention, it will be instructive to engage in brief review of the published literature dealing with human clinical trials conducted with administered in a parenteral manner. Physicochemical studies of CPT found that the closed E-ring lactone form of CPT possessed extremely poor solubility in water (i.e., approximately 0.1 µg of drug dissolving in 1 mL of water). In addition, of the two CPT enantiomers, the naturally occurring (S)-isomer was found to be more potent than the (R)-isomer. See, e.g., Motwani, M. V., et al., Flavopiridol (Flavo) Potentiates the SN-38-Induced Apoptosis in Association with Downregulation of Cyclin Dependent Kinase Inhibitor p21waf1/cip1 in HCT116 Cells. *Proc. Am. Assoc. Cancer Res.* 41:32-43 (2000). These different properties of the various analogs are caused by the different chemical substituents on the core structure of CPT.

Thus, because of its extremely poor water solubility, in order for CPT to be administered in human clinical trials, it was initially formulated using sodium hydroxide. It is important to note, that all of these early clinical studies used sodium hydroxide formulations of CPT in order to markedly increase the water solubility (i.e., hydrophilicity) of the molecule to allow sufficient quantities of the agent to be administered parenterally to patients. The sodium hydroxide formulation of CPT created more water soluble CPT species that permitted clinicians to administer larger concentrations of CPT with smaller medication volumes of administration, thereby allowing sufficiently higher doses of the drug to be administered to cancer subjects undergoing Phase I and Phase II clinical trials. However, it was subsequently established that this formulation resulted in hydrolysis of the lactone E-ring of the camptothecin molecule, thus forming the water soluble carboxylate form of CPT which only possessed approximately one-tenth or less of the anti-tumor potency of the original, non-hydrolyzed lactone form of CPT. The clinical trials performed using the sodium hydroxide-formulated CPT provide to be highly disappointing, due to both the frequently-observed significant systemic toxicities and the lack of anti-neoplastic activity. It was subsequently ascertained that the drug's relative low hydrophilicity, was the most important reason for these side-effects. This low aqueous solubility of CPT in the lactone form greatly limited the practical clinical utility of the drug because prohibitively large volumes of fluid had to be administered to the subject in order to provide an effective dose of the drug. Because of the potent anti-neoplastic activity and poor water solubility of CPT lactone forms and many of its analogs in water, a great deal of effort was directed at generating new CPT lactone analogs that possessed greater aqueous solubility. Water soluble CPT analogs should not exist in large amounts in the open E-ring form but, alternately, should predominantly remain in the closed-ring lactone form, in order to be active. Thus, CPT analogs where equilibrium favors the closed-ring lactone form are desirable for administration.

II. Pharmacological Activity of CPT

Despite these earlier disappointing side-effects, increasing clinical interest in CPT was evoked during the 1980s, as a result of the revelation of its mechanism of action (i.e., Topoisomerase I inhibition). This new information regarding the mechanism of action of CPT analogs served to rekindle the interest in developing new Topoisomerase I inhibitors for use as anti-neoplastic drugs and subsequently several research groups began attempting to develop new CPT analogs for cancer therapy. See, Hsiang, Y. H., et al., Camptothecin Induces Protein-Linked DNA Breaks Via Mammalian DNA Topoisomerase I. *J. Biol. Chem.* 260:14873-14878 (1985); Hsiang, Y. H.; Liu, L. F., Identification of Mammalian DNA Topoisomerase I as an Intracellular Target of the Anticancer Drug Camptothecin. *Cancer Res.* 48:1722-1726 (1988); Hsiang, Y. H., et al., Arrest of Replication Forks by Drug- Stabilized Topoisomerase I DNA Cleavable Complexes as a Mechanism of Cell Killing by Camptothecin. *Cancer Res.* 49:5077-5082 (1989).

Several clinically important anticancer drugs kill tumor cells by affecting DNA Topoisomerases. Topoisomerases are essential nuclear enzymes that function in DNA replication and tertiary structural modifications (e.g., overwinding, underwinding, and catenation) which normally arise during replication, transcription, and perhaps other DNA processes. Two major Topoisomerases that are ubiquitous to all eukaryotic cells: (i) Topoisomerase I (Topo I) which cleaves single stranded DNA and (ii) Topoisomerase II (Topo II) which cleaves double stranded DNA. Topoisomerase I is involved in DNA replication; it relieves the torsional strain introduced ahead of the moving replication fork.

Topoisomerase I (Topo I) is a monomeric 100 kDal polypeptide containing 765 amino acids, and is encoded by a gene located on chromosome 20q12-13.2. See, e.g., Creemers, G. J., et al., Topoisomerase I Inhibitors: Topotecan and Irinotecan. *Cancer Treat. Rev.* 20:73-96 (1994); Takimoto, C. H.; Arbuck, S. G. The Camptothecins. *Cancer Chemother and Biother.* $2^{nd}$ edition (B. L. Chabner, D. L. Longo (eds)), 463-384 (1996). It is an essential enzyme in DNA replication and RNA transcription, and is present in all eukaryotic (including tumor) cells. Since normal DNA is super-coiled, and tightly fitted in the chromosomes, the DNA-replication fork is unable to synthesize new DNA out of this topological constrained DNA. Topo I acts in an ATP-independent fashion, by binding to super-coiled DNA and cleaving a phosphodiester bond, resulting in a single-strand break. At the same time, Topo I forms a covalent reversible adduct between a tyrosine residue at position 723 of Topo I and the 3' end of the single-strand DNA molecule, called the cleavable complex. The DNA molecule is able to rotate freely around the intact single DNA strand, and relaxation of the DNA occurs. After the religation of the cleavage, Topo I dissociates from the DNA. The cleavable complex usually is present for only a short time, just to allow the single uncleaved DNA strand to unwind.

Specifically, it was found that CPT forms a reversible complex comprising: Topo I-CPT-DNA. In brief, the primary mechanism of action of CPT is the inhibition of Topo I by blocking the rejoining step of the cleavage/relegation reaction of Topo I, thus resulting in the accumulation of covalent reaction intermediates (i.e., the cleavable complex). CPT-based cellular apoptosis is S-phase-specific killing through potentially lethal collisions between advancing replication forks and Topo I DNA complexes. Two repair responses to Topo I-mediated DNA damage involving covalent modification of Topo I have been identified. The first involves activation of the Ubiquitin/26S proteasome pathway, leading to degradation of Topo I (CPT-induced Topo I down-regulation). The second involves the Small Ubiquitin-like Modifier (SUMO) conjugation to Topo I. These repair mechanisms for Topo I-mediated DNA damage play an important role in determining CPT sensitivity/resistance in tumor cells.

Topo I purified from human colon carcinoma cells or calf thymus has been shown to be inhibited by CPT. CPT, Irinotecan™ (CPT-11) and an additional Topo I inhibitor, Topotecan™, has been in used in clinical trials to treat certain types of human cancer. For the purpose of this invention, CPT analogs include: 7-ethyl-10-[4-(1-piperidino)-1-piperidino] carbonyloxy camptothecin (Irinotecan™ or CPT-11), 10-hydroxy-7-ethyl camptothecin (HECPT), 9-aminocamptothecin, 10,11methylenedioxy camptothecin and 9-dimethylaminomethyl-10-hydroxy camptothecin (Topotecan™). These CPT analogs use the same mechanism to inhibit Topo I; they stabilize the covalent complex of enzyme and strand-cleaved DNA, which is an intermediate in the catalytic mechanism. These analogs have no binding affinity for either isolated DNA or Topo I but do bind with measurable affinity to the enzyme-DNA complex. The stabilization of the Topo I "cleavable complex" by CPT and analogs is readily reversible.

Topoisomerase II (Topo II) works in a similar way to Topo I, with the difference being that the former enzyme acts ATP-dependently, to cause reversible doublestrand DNA cleavage, in the relaxation of DNA. Direct interference of CPTs with Topo II has not been described. However, it has been reported that Irinotecan™ (CPT-11) treatment sensitizes some tumor-xenografts in mice to Topo II inhibitors, by increasing the Topo II mRNA expression after 24 and 48 hours. This suggests that combination therapies with Topo I and Topo II targeting chemotherapy for human solid tumors might be valuable. The CPT analogs inhibit the religation reaction of Topo I by selectively inducing a stabilization of the cleavable complexes at Topo I sites bearing a guanine residue at the 5'-terminus of the enzyme mediated breaks. See, e.g., Svejstrup, J. Q., et al., Technique for Uncoupling the Cleavage and Religation Reactions of Eukaryotic Topoisomerase I. The Mode of Action of Camptothecin at a Specific Recognition Site. *J. Mol. Biol.* 222:669-678 (1991); Jaxel, C., et al., Effect of Local DNA Sequence on Topoisomerase I Cleavage in the Presence or Absence of Camptothecin. *J. Biol. Chem.* 266: 20418-20423 (1991); Tanizawa, A., et al., Induction of Cleavage in Topoisomerase I c-DNA by Topoisomerase I Enzymes From Calf Thymus and Wheat Germ in the Presence and Absence of Camptothecin. *Nucl. Acids Res.* 21:5157-5166 (1994). Although this stabilization in itself is reversible, an irreversible doublestrand break occurs when a replication fork meets a cleavable complex. The higher the levels of Topo I, the higher the frequency of cleavable complexes, and the higher the number of DNA breaks. These breaks may lead to cell cycle arrest in the S/G2-phase, activation of apoptosis pathways, and finally to cell death. See, e.g., Hsiang, Y. H., et al., Arrest of Replication Forks by Drug-Stabilized Topoisomerase I DNA Cleavable Complexes as a Mechanism of Cell Killing by Camptothecin. *Cancer Res.* 49:5077-5082 (1989). As a result of this, Topo I inhibitors are only lethal in the presence of ongoing DNA replication or RNA transcription. See, e.g., D'Arpa, P., et al., Involvement of Nucleic Acid Synthesis in Cell Killing Mechanisms of Topoisomerase I Poisons. *Cancer Res.* 50:6919-6924 (1990). S-phase synchronized cells appeared to be much more sensitive to Topo I inhibitors, compared to G1- or G2/M-cells, suggesting an S-phase specific cytotoxicity for this type of drugs. See, e.g., Takimoto, C. H., et al., Phase I and Pharmacologic Study of Irinotecan Administered as a 96-Hour Infusion Weekly to Adult Cancer Patients. *J. Clin. Oncol.* 18:659-667 (2000). In colon, prostate, ovary and esophagus tumors, elevated Topo I levels have been found, whereas in kidney tumors and non-Hodgkin lymphomas this was not the case See, e.g., Van der Zee, A., et al., P-glycoprotein Expression and DNA Topoisomerase I and II Activity in Benign Tumors of the Ovary and in Malignant Tumors of the Ovary, Before and After Platinum/Cyclophosphamide Chemotherapy. *Cancer Res.* 51: 5915-5920 (1991). Recent investigations have indicated that Irinotecan™ and Topotecan™ are also inhibitors of angiogenesis, a property that might contribute to their chemotherapeutic activity. Neovascularization has been positively correlated with increasing invasion and metastases of various human tumors. In mice cornea models, anti-angiogenic effects of some CPTs, including Irinotecan™ (CPT-11), were studied. Angiogenesis was induced by fibroblast growth factor, but by increasing the dose of Irinotecan™, the area of angiogenesis in the tumor decreased, following a negative, almost exponential, curve. At dose levels of 210 mg/kg a significant reduction of neovascularization was observed.

Although CPT and the aforementioned CPT analogs have no discernable direct effects on Topo II, these CPT analogs are believed to stabilize the Topo I "cleavable complex" in a manner analogous to the way in which epipodophyllotoxin glycosides and various anthracyclines inhibit Topo II.

Inhibition of Topo I by CPT and analogs induces protein-associated-DNA single-strand breaks. Virtually all of the DNA strand breaks observed in vitro cells treated with CPT are protein linked. However, an increase in unexplained protein-free breaks can be detected in L1210 cells treated with CPT. The analogs appear to produce identical DNA cleavage patterns in end-labeled linear DNA. It has not been demonstrated that CPT or CPT analogs cleaves DNA in the absence of the Topo I enzyme.

III. Cell Cycle-Specific Activity of Camptothecin

The activity of CPT is cell cycle-specific. The greatest quantitative biochemical effect observed in cells exposed to CPT is DNA single-strand breaks that occur during the S-phase. Because the S-phase is a relatively short phase of the cell cycle, longer exposure to the drugs results in increased cell killing. Brief exposure of tumor cells to the drugs produces little or no cell killing, and quiescent cells are refractory. These aforementioned results are likely due to two factors:

(i) This class of drugs inhibit the normal activity of Topo I, reversibly. Although they may produce potentially lethal modifications of the DNA structure during DNA replication, the DNA strand breaks may be repaired after washout of the drug; and (ii) Cells treated with Topo I inhibitors, such as CPT tend to stay in $G_0$ of the cell cycle until the drug is removed and the cleaved DNA is repaired. Inhibitors of these enzymes can affect many aspects of cell metabolism including replication, transcription, recombination, and chromosomal segregation.

IV. Previously-Tested Camptothecin Analogs

As discussed above, CPT and many of its analogs (see e.g., Wall and Wani, Camptothecin and Taxol: Discovery to Clinic-Thirteenth Bruce F. Cain Memorial Award Lecture *Cancer Research* 55:753-760 (1995)) are poorly water soluble and are reportedly also poorly soluble in a number of pharmaceutically-acceptable organic solvents as well. However, there are numerous reports of newly created water soluble analogs of CPT (Sawada, S., et al., Synthesis and Antitumor Activity of Novel Water Soluble Analogs of Camptothecin as Specific Inhibitors of Topoisomerase I. *Jour. Med. Chem.* 38:395-401 (1995)) which have been synthesized in an attempt to overcome some of the significant technical problems in drug administration of poorly water soluble camptothecins to subjects with cancer. Several water soluble CPT analogs have been synthesized in an attempt to address the poor water solubility and difficulties in administration to subjects. Several examples of these water soluble CPT analogs are set forth below in Table I:

TABLE I 9-dimethylaminomethyl-10-hydroxycamptothecin (Topotecan ™)
7-[(4-methylpiperazino)methyl]-10,11-ethylenedioxycamptothecin
7-[(4-methylpiperazino)methyl]-10,11-methylenedioxycamptothecin
7-ethyl-10-[4-(1-piperidino)-1-piperidino]carbonyloxycamptothecin (Irinotecan ™ or CPT-11)
9-nitrocamptothecin (Rubitecan)

Other substituted CPT analogs with different solubility and pharmacologic properties have been synthesized as well; examples of these camptothecin analogs include 9-aminocamptothecin and 9-nitrocamptothecin (Rubitecan) that are poorly soluble in both aqueous and non-aqueous media and have been tested in humans. Rubitecan (9-nitrocamptothecin) is a prodrug of 9-aminocamptothecin, and has been shown to spontaneously convert to 9-aminocamptothecin in aqueous media and in vivo in mice, dogs and humans (see, Hinz, et al., Pharmacokinetics of the in vivo and in vitro Conversion of 9-Nitro-20(S)-camptothecin to 9-Amino-20 (S)-camptothecin in Humans, Dogs and Mice, *Cancer Res.* 54:3096-3100 (1994)).

The pharmacokinetic behavior of 9-nitrocamptothecin and 9-aminocamptothecin is similar to the water-soluble camptothecin analogs (i.e., Topotecan™ and Irinotecan™) in that the plasma half lives are markedly shorter than the more lipid soluble CPT analogs. An additional major problem with 9-aminocamptothecin is that its chemical synthesis using the semi-synthetic method is performed by nitration of CPT, followed by reduction to the amino group, which is a very low yield type of synthesis. 9-aminocamptothecin is also light sensitive, heat sensitive and oxygen sensitive which render both the initial synthesis and subsequent stability (i.e., shelf-life) of 9-aminocamptothecin problematic, at best. Moreover, the chemical decomposition reactions of 9-aminocamptothecin frequently result in the formation of analogs that exhibit a large degree of toxicity in nude mice, whereas pure 9-aminocamptothecin is significantly less toxic.

As previously discussed, 9-aminocamptothecin is also difficult to administer to subjects because it is poorly soluble in both aqueous and organic solvents. Alternately, while 9-nitrocamptothecin is easier to produce and is more chemically stable, the chemical conversion to 9-aminocamptothecin causes the drug is reportedly susceptible to MDR/MRP tumor-mediated drug resistance, which further limits its utility in the unfortunately common setting of drug resistant neoplasms. Based on pharmacokinetic behavior and chemical properties, 9-aminocamptothecin is predicted to have reduced tissue penetration and retention relative to more lipid soluble camptothecin analogs. Further, its poor solubility diminishes the amount of the drug that can cross the blood/brain barrier.

Of this diverse group of substituted CPT analogs undergoing human clinical development, Irinotecan™ (CPT-11) has been one of the most extensively studied in both Phase I and Phase II clinical trials in human patients with cancer. It is noteworthy that 7-ethyl-10-[4-(1-piperidino)-1-piperidino] carbonyloxy camptothecin (Irinotecan™), which is a water soluble prodrug, is biologically inactive and requires activation by a putative carboxylesterase enzyme. The active species of Irinotecan™ is the depiperidenylated 10-hydroxy-7-ethyl camptothecin (as claimed in Miyasaka, et al., U.S. Pat. No. 4,473,692, (1984)), which is also known as SN38. SN38 is a toxic lipophilic metabolite, which is formed by an in vivo bioactivation of Irinotecan™ by a putative carboxylesterase enzyme.

SN38 is very poorly soluble in water and has not been directly administered to human patients with cancer. Recently, it has been reported in human patients that SN38 undergoes further metabolism to form a glucuronide species, which is an inactive form of the drug with respect to antitumor activity, and also appears to be involved in producing human toxicity (e.g., diarrhea, leukopenia) and substantial interpatient variability in drug levels of the free metabolite and its glucuronide conjugate.

Irinotecan™ has been tested in human clinical trials in the United States, Europe and Japan. Clinical studies in Japan alone, have reported approximately 100 patient deaths which have been directly attributable to Irinotecan™ drug toxicity. The Miyasaka, et al. patents (U.S. Pat. No. 4,473,692 and U.S. Pat. No. 4,604,463) state that the object of their invention is to " . . . provide 10-substituted camptothecins which are strong in anti-tumor activity and possess good absorbability in living bodies with very low toxicity" and " . . . to provide new camptothecin analogs which are strong in anti-tumor activity and possess good solubility in water and an extremely low toxicity".

Having multiple drug-related human deaths and serious patient toxicity, is clearly a failure of the aforementioned 10-substituted camptothecins synthesized by Miyasaka, et al., to fulfill their stated objectives. It is notable that tremendous interpatient variability with regard to drug levels of various forms, drug metabolism, certain pharmacokinetic properties and toxicity has been reported with the use of Irinotecan™ in human subjects with cancer. Parenteral administration of Irinotecan™ can achieve micromolar plasma concentrations of Irinotecan™ that, through metabolism to form SN38, can yield nanomolar concentrations of the active metabolite SN38. It has recently been reported in human subjects that SN38 undergoes further metabolism to form the SN38 glucuronide (see, e.g., Gupta, et al., Metabolic Fate of Irinotecan in Humans: Correlation of Glucuronidation with Diarrhea. *Cancer Res.* 54:3723-3725 (1994)).

This further metabolic conversion of Irinotecan™ is important, since there is also reportedly large variability in the conversion of Irinotecan™ to SN38 and large interpatient variability in the metabolism of SN38 to form the inactive (and toxic) SN38 glucuronide conjugate in human subjects. (see, e.g., Gupta, et al., Metabolic Fate of Irinotecan in Humans: Correlation of Glucuronidation with Diarrhea. *Cancer Res.* 54:3723-3725 (1994) and Ohe, et al., Phase I Study and Pharmacokinetics of CPT-11 with 5-Day Continuous Infusion. *JNCI* 84(12):972-974 (1992)).

Since the amount of Irinotecan™ and SN38 metabolized is not predictable in individual patients, significant clinical limitations are posed and create the risk of life-threatening drug toxicity, and/or risk of drug inactivity due to five putative biological mechanisms: (i) conversion of greater amounts of Irinotecan™ to SN38; (ii) inactivation of SN38 by glucuronidation; (iii) conversion of SN38 glucuronide to free SN38; (iv) lack of anti-neoplastic activity due to the conversion of lesser amounts of Irinotecan™ to form SN38; and (v) lack of anti-neoplastic activity by more rapid and extensive conversion of SN38 to form the glucuronide species. It is important to note that even a doubling of the plasma concentration of the potent Irinotecan™ metabolite SN38 may result in significant toxicity, because free SN38 exhibits anti-neoplastic activity at nanomolar concentrations.

Another source of interpatient variability and toxicity is the in vivo de-glucuronidation of SN38 and similar CPT analogs to produce a free and active species of the drug. Deglucuronidation of a CPT analog that is susceptible to A-ring glucuronidation, such as SN38, results in an increase in the plasma or local tissue concentration of the free and active form of the drug, and if high enough levels were reached, patient toxicity, and even death may result.

In addition to the two aforementioned FDA-approved drugs, there are currently at least nine camptothecin analogs that have been evaluated in various stages of clinical testing. These camptothecin analogs include:

1. Karenitecin® (BNP1350)

Karenitecin® (BNP1350) is a highly lipophilic camptothecin analog having a 7-trimethylsilylethyl moiety and is claimed in U.S. Pat. No. 5,910,491, along with formulations and uses thereof. Formulations of Karenitecin® with N-methylpyrrolidinone (NMP) are claimed in, e.g., U.S. Pat. No. 5,726,181.

2. Lurtotecan (NX 211)

NX211 is a water-soluble camptothecin having a 10,11-ethylenedioxy moiety and a cleavable 4-methylpiperazino methyl moiety at C7. By way of example, U.S. Pat. No. 5,559,235 discloses and claims the analogs and formulations, and uses thereof.

3. Exatecan (DX-8951f)

DX-8951f is a hexacyclic camptothecin analog, having 10-methyl and 11-fluoro substitutions, and with its sixth ring fused between C7 and C9. By way of example, and not of limitation, U.S. Pat. No. 5,637,770 describes and claims the analog, and formulations and uses thereof.

4. Diflomotecan (BN 80915)

BN 80915 is a 10,11-difluorocamptothecin, with a 7-member E-ring. By way of example, and not of limitation, U.S. Pat. No. 5,981,542 describes and claims the analog, and its uses and formulations.

5. Rubitecan (9-Nitro CPT)

9-Nitrocamptothecin, as mentioned above is poorly soluble in both aqueous and organic solvents and is described and is not claimed any United States Patents, with the first publication of the analog occurring in Japanese Patent Application No. 82-160944 in 1982. Several patents have issued since then, all regarding processes for preparing the analog as well as uses thereof.

5. Afeletecan (CPT Glycoconjugate)

Afeletecan is an C20 glycoconjugated, water-soluble analog of camptothecin and is described and claimed in U.S. Pat. No. 6,492,335.

6. Gimatecan (ST1481)

ST1481 is a non-water-soluble camptothecin derivative having a C7 imino moiety, bonded to a terminal tert-butoxy group. The analog is described and claimed in U.S. Pat. No. 6,242,457.

8. Mureletecan (PNU 166148)

Mureletecan is another water-soluble prodrug having a cleavable peptide moiety bonded to C20 to form an ester.

9. Pegbetotecan, Pegcamotecan, Peglinxotecan (PEG CPT; Prothecan®)

This prodrug includes a cleavable water-soluble polyethylene glycol moiety that forms an ester at C20. By way of example, the analog is described and claimed in U.S. Pat. No. 5,840,900.

The various chemical structures of the nine aforementioned camptothecin analogs are set forth in Table II, below:

TABLE II
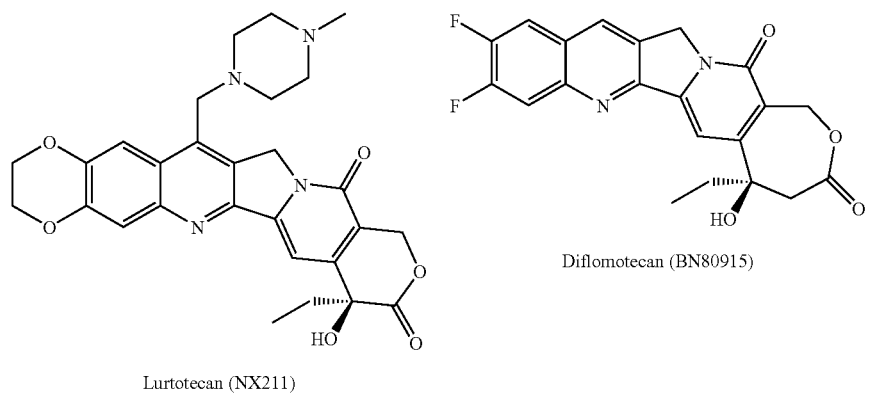
Lurtotecan (NX211)
Diflomotecan (BN80915)
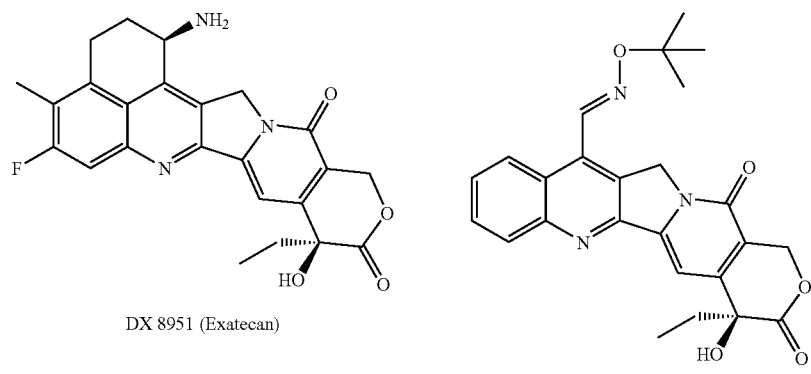
DX 8951 (Exatecan)
Gimatecan (ST1481)
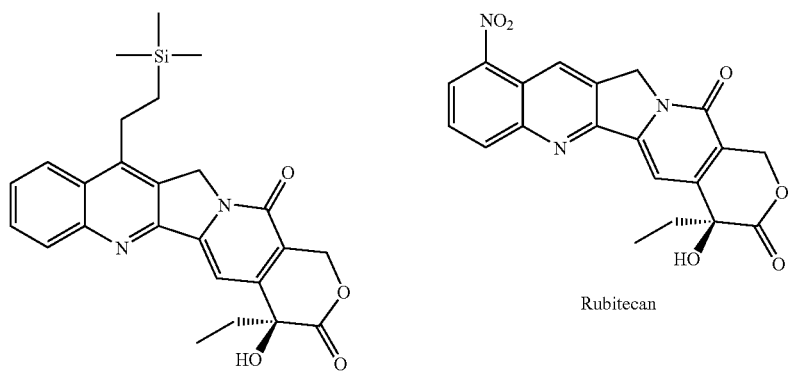
BNP 1350
Rubitecan TABLE II-continued

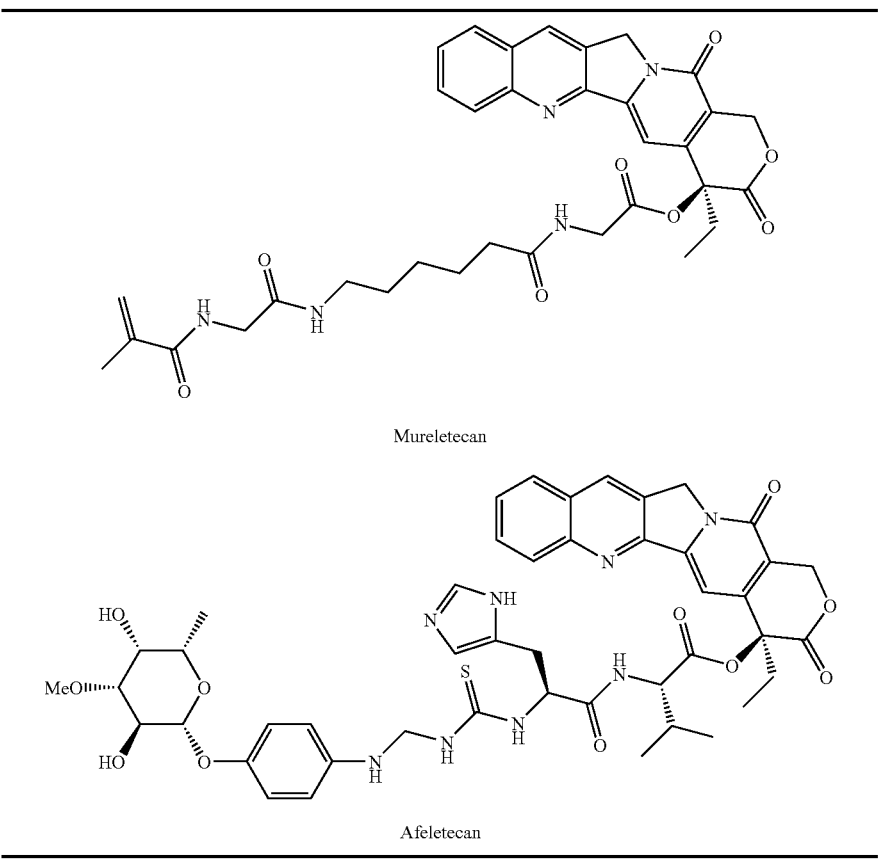

Mureletecan

Afeletecan

Poorly water-soluble (i.e., hydrophobic) camptothecins are necessarily formulated for administration by dissolution or suspension in organic solvents. U.S. Pat. No. 5,447,936; No. 5,726,181; No. 5,859,022; No. 5,859,023; No. 5,880,133; No. 5,900,419; No. 5,935,967; No. 5,955,467; and other describe pharmaceutical formulations of highly lipophilic, poorly water-soluble camptothecin analogs in various organic solvents, namely N,N-dimethylacetamide (DMA); N,N-dimethylisosorbide (DMI); and N-methylpyrrolidinone (NMP).

VI. Formulation and Administration of CPT and Analogs

In the early-1970's, clinical studies utilizing the sodium salt of camptothecin were begun at the Baltimore Cancer Research Center. In this clinical trial, CPT was administered as a rapidly running IV solution over a 5-10 minute period at a concentration of 2 mg of camptothecin sodium per milliliter of saline. Doses of CPT sodium from 0.5 to 10.0 mg/kg of actual or ideal body weight (whichever was less) were used. These investigators reported that because hemorrhagic sterile cystitis was noted in several of the early trials, patients receiving camptothecin sodium were well-hydrated either intravenously (i.v.) or orally for 72 hours after drug administration. It is noteworthy that the mean urine recovery of CPT was 17.4% over the first 48 hours (with the range from: 3.6% to 38.9%) with most of the excretion occurring in the initial 12 hours. When these investigators excluded the five patients with impaired excretion, the mean urine recovery of CPT was 22.8%. These investigators noted that non-metabolized camptothecin in high concentrations rapidly appeared in the urine after iv drug administration and went further to state that this finding probably accounted for the sterile hemorrhagic cystitis noted in three moderately dehydrated patients. Although maintaining a copious urine outflow seems able to prevent this complication, the investigators reported that they were exploring various alterations in urine pH as another possible way of decreasing the risk of this debilitating type of toxicity.

Muggia, et. al. (Phase I Clinical Trial of Weekly and Daily Treatment with Camptothecin (NSC-100880): Correlation with Preclinical Studies. *Cancer Chemotherapy Reports, Part* 1. 56(4):515-521 (1972)) reported results of a Phase I clinical trial in fifteen patients treated with CPT sodium at four weekly dose levels ranging from 20-67 mg/m$^2$. No clinical benefit was observed in eight patients with measurable disease who were treated with the 5-day courses at dose levels associated with toxicity. The CPT was administered in concentrations of 1 or 10 mg/mL and it was always administered by intravenous push. Cystitis was the most prominent non-hematologic toxic effect observed in this study. Bladder toxicity was dose limiting in three patients receiving doses of 20 to 30 mg/m$^2$, and occurred in two additional patients at doses of 30 and 44 mg/m$^2$. Cystitis, another toxic effect occurring frequently after treatment with camptothecin, was not predicted by preclinical toxicological studies. Clinical experience present inventors would suggest that the occurrence of cystitis may be related to the duration of the patient's exposure to the drug. It is their experience that CPT is excreted unchanged by the kidneys, although a large percentage of the drug administered cannot be accounted for in the urine. It is possible that relatively less drug is excreted in the urine of animals since an extremely active transport of CPT into bile has been demonstrated. Alternatively, one needs to postulate that the mucosa of the human bladder is more susceptible to the toxic action of CPT or that the effect on the human bladder is due to some unrecognized CPT metabolite.

In 1972, Moertel and coworkers (Phase II study of camptothecin (NSC-100880) in the treatment of advanced gastrointestinal cancer. *Cancer Chemother Rep.* 56(1):95-101 (1972)) administered CPT sodium dissolved in physiologic saline at a concentration of 2 mg/mL and administered by rapid intravenous infusion over 5-10 minutes. Two schedules of administration were used in this study: (i) a single injection repeated at 3-week intervals; and (ii) a 5-day course repeated every 4 weeks. The initial dose for the single-dose method was 180 mg/m$^2$. Because of toxic effects, which were considered excessive by the investigators, later patients were treated at doses ranging between 90 and 120 mg/m$^2$. Dosages for the 5-day course ranged between 11 and 22 mg/m$^2$/day (total course: 55-110 mg/m$^2$). The toxicity and response data from this aforementioned study is summarized, below, in Table III-Table VI. Diarrhea was only a problem at higher doses, although it could be quite severe to the point of fecal incontinence and could persist for as long as 4 weeks. Cystitis usually began about 7-10 days after treatment and was characterized clinically by dysuria and frequency. With more severe toxicity, gross hematuria developed. Pathologically, this was characterized by multiple necrotic ulcerations which could involve the entire urinary tract from kidney pelvis to bladder. According to these investigators, the occurrence of hemorrhagic cystitis did not preclude further treatment with CPT, and its severity could be titrated down by lowering the dose in subsequent courses. These investigators also reported that the more prolonged schedule produced more severe toxicity at a given total dose level, but the difference was not as great as might have been predicted by preclinical animal studies.

These investigators proposed that a reasonable initial dose of CPT sodium is 110-120 mg/m$^2$ for the single-injection method or 17 mg/m$^2$/day (total dose: 85 mg/m$^2$) for the 5-day course. They noted that after 2 months (8 or 9 weeks) only two of their 61 patients showed evidence of partial objective improvement and none showed improvement at 3 months. Both patients who demonstrated an objective response at 2 months had large bowel cancer. These investigators concluded that CPT " . . . is a drug of protean and unpredictable toxicity that has no clinical value in the management of gastrointestinal cancer."

TABLE III

Toxic Reactions: Single-Dose Method
Number of Patients with Non-Hematologic Toxicity:

| Dose (mg/m$^2$) | No. of Patients Treated | Diarrhea | Cystitis |
|---|---|---|---|
| 90 | 10 | | |
| 100 | 6 | | 2 |
| 110 | 2 | 1 | 1 |
| 120 | 7 | 4 | 2 |
| 180 | 9 | 2 | 3 |

TABLE IV

Toxic Reactions: 5-day Course
Non-Hematologic Toxicity No. of Patients With:

| Dose (mg/m$^2$ × 5) | No. of Patients Treated | Diarrhea | Cystitis |
|---|---|---|---|
| 11 | 2 | | 1 |
| 15 | 9 | 1 | 4 |
| 17 | 5 | 4 | 2 |
| 20 | 10 | 4 | 6 |
| 22 | 1 | 1 | |

TABLE V

Relationship of Method of Administration to Cystitis

| | Method of Administration | |
|---|---|---|
| Cystitis | Single Dose (% of 34 Patients) | 5-Day Course (% of 27 Patients) |
| | 24 | 48 (P < 0.05) |

TABLE VI

Objective Results

Single-Dose Method (34 Patients Total)

| | Time after start of therapy | | | |
|---|---|---|---|---|
| Objective Results* | 3 wks | 6 wks | 9 wks | 12 wks |
| Improved | 4 | 2 | 2 | — |
| Stable | 17 | 11 | 8 | 6 |
| Worse | 13 | 21 | 24 | 28 |

5-Day Course (27 Patients Total)

| | Time after start of therapy | | |
|---|---|---|---|
| Objective results* | 4 wks | 8 wks | 12 wks |
| Improved | 1 | — | — |
| Stable | 12 | 7 | 6 |
| Worse | 14 | 20 | 21 |

*A total of 3 patients showed a 25%-50% response at 3 wks, only.

In another study, Gottlieb and Luce (Treatment of Malignant Melanoma with Camptothecin (NSC-100880) *Cancer Chemotherapy Reports*, Part 1 56(1):103-105 (1972)) reported the results of treatment of patients with malignant melanoma with CPT sodium (1972). Fifteen patients with advanced malignant melanoma were treated with CPT at doses of 90-360 mg/m$^2$ repeated every 2 weeks. CPT-sodium was administered as a single rapid intravenous (IV) injection starting at a dose of 120 mg/m$^2$ repeated at 2-week intervals. The dose in subsequent courses was increased by increments of 60 mg/m$^2$ per dose (to a maximum of 360 mg/m$^2$) in eight patients who tolerated their initial doses with minimal toxicity. To prevent the known bladder toxicity of this drug, patients were well hydrated for 3 days after therapy. None of the patients had a 50% or greater decrease in tumor diameter. Less pronounced transient tumor regression was noted in three patients, but no clinical benefit was associated with these responses. The remaining patients had no change or progression in their disease. Toxic effects included myelosuppression (11 patients), nausea and vomiting, alopecia, diarrhea, and hemorrhagic cystitis. These investigators concluded that CPT, at least as administered in this study, had little to offer the patient with advanced disseminated melanoma.

Creaven, et al., (Plasma Camptothecin (NSC-100880) Levels During a 5-Day Course of Treatment: Relation to Dose and Toxicity. *Cancer Chemotherapy Reports Part* 1 56(5): 573-578 (1979)) reported studies of plasma CPT levels during a 5-day course of treatment. These investigators state that the toxicity of CPT has been widely and unpredictably variable in the course of initial clinical evaluation. Severe toxic effects occurred even though patients with obvious renal disease were excluded. In this study they investigated plasma CPT levels 24 hours after the administration of sodium CPT administered on a once daily over a 5 day total schedule to determine whether such measurements would be of value in predicting toxicity, and observed that plasma CPT levels have little relation to the dose given when the dose is in the range of 6.5-20 mg/m²/day.

There are several features which establish a commonality with these aforementioned studies with those utilizing sodium CPT. First, is the use of sodium-CPT which made the CPT more water soluble by hydrolysis of lactone E ring to form the carboxylate species (i.e., by formulating CPT in sodium hydroxide). The anti-tumor activity of the carboxylate form of CPT is reduced by at least 10-fold, which partially accounts for the lack of clinical response in these studies. Second, is the rapid intravenous administration of the drug. CPT is an S-phase specific drug and therefore will exert a greater chemotherapeutic effect under conditions of prolonged exposure, as in a continuous intravenous infusion. The short infusion (i.v. "push" or rapid i.v. infusion) times in all of these studies do not allow a long enough exposure time to the drug at suitable levels, and is further compounded by the administration of the water soluble carboxylate form of CPT. A third common feature is the notable frequency of cystitis in these studies using sodium CPT.

SUMMARY OF THE INVENTION

There remains a need for camptothecin analogs which, for example, (i) are highly lipophilic; (ii) possess substantial lactone stability; (iii) possess a long plasma half-life; (iv) reduce drug-binding affinity to plasma proteins; (v) increase the amount of free drug in human plasma which will improve the drug's bioavailability of the parent compound; (vi) augment intracellular drug uptake; and decrease to formation of glucuronide species (glucuronidation), which is an inactive form of the drug with respect to anti-tumor activity.

The camptothecin analogs disclosed and claimed in the present invention represent a novel class of chemotherapeutic compounds that have exhibited potent antineoplastic activity against common types of cancer including but not limited to cancers of the lung, breast, prostate, pancreas, head and neck, ovary, colon, as well as melanoma. While the camptothecin analogs disclosed in the instant invention possess Topoisomerase I inhibitory activity similar to that of other camptothecin derivatives, they also possess novel structural modifications which are rationally designed for superior bioavailability and tissue penetration, while concomitantly avoiding untoward metabolism and drug resistance mechanisms which are common in human and other mammalian cancers.

The present invention discloses, in a non-limiting manner, analogs of the anti-tumor agent Karenitecin®, and pharmaceutically-acceptable salts thereof, wherein various types of covalent linkages will connect the novel side chain at the C10 position on the A-ring of the Karenitecin® molecule. However, it should be noted that the silicon of Karenitecin® may also be substituted with germanium. These analogs are amphipathic and exploit the novel polar side chains to decrease protein binding and to augment intracellular uptake/tissue retention. The polar group on the side chain of these novel Karenitecin® analogs will reduce drug-binding affinity to plasma proteins, so as to improve plasma protein binding properties while concomitantly maintaining both lactone stability and drug potency. The increased free (i.e., non-plasma protein bound) drug in human plasma will improve the bioavailability of the parent compound. Moreover, as previously discussed, the hydrolysis of the lactone E-ring of either the camptothecin/Karenitecin® molecule (thus forming the water soluble carboxylate form) only possesses approximately one-tenth or less of the anti-tumor potency of the original, non-hydrolyzed closed lactone E-ring form of the camptothecin/Karenitecin® molecule.

The analogs of the present invention have significant utility as highly efficacious chemotherapeutic drugs, and are significantly less toxic than previously disclosed camptothecin derivatives. The new analogs also do not undergo A-ring or B-ring glucuronidation (and implicitly deglucuronidation), and they are not prodrugs requiring metabolic activation. Furthermore, the lack of glucuronidation decreases deleterious physiological side-effects (e.g., diarrhea, leukopenia) and may also mitigate substantial interpatient variability in drug levels of the free metabolite and its glucuronide conjugate.

Thus, in summation, the novel Karenitecin® analogs, and pharmaceutically-acceptable salts thereof, of the present invention: (i) possess potent antitumor activity (i.e., in nanomolar or subnanomolar concentrations) for inhibiting the growth of human and animal tumor cells in vitro; (ii) are potent inhibition of Topoisomerase I; (iii) lack of susceptibility to MDR/MRP drug resistance; (iv) require no metabolic drug activation: (v) lack glucuronidation of the A-ring or B-ring; (vi) reduce drug-binding affinity to plasma proteins; (vii) maintain lactone stability; (viii) maintain drug potency; and (ix) possess a low molecular weight (e.g., MW<600).

It is an object of the present invention to provide fascile and extremely efficient synthetic methodologies for the preparation of novel C10-substituted Karenitecin® analogs.

Another object is to provide new and useful Karenitecin® analogs which are highly efficacious as chemotherapeutic agents.

Other objects will become apparent from a reading of the following Specification and Claims.

DETAILED DESCRIPTION OF THE INVENTION

Definitions

"Scaffold" means the fixed structural part of the molecule of the formula given.

"Fragments", "Moieties" or "Substituent Groups" are the variable parts of the molecule, designated in the formula by variable symbols, such as $R_x$, X or other symbols. Fragments may consist of one or more of the following:

"$C_x$-$C_y$ alkyl" generally means a straight or branched-chain aliphatic hydrocarbon containing as few as x and as many as y carbon atoms. Examples include "$C_1$-$C_6$ alkyl" (also referred to as "lower alkyl"), which includes a straight or branched chain hydrocarbon with no more than 6 total carbon atoms, and $C_1$-$C_{16}$ alkyl, which includes a hydrocarbon with as few as one up to as many as sixteen total carbon atoms, and the like. In the present application, the term "alkyl" is defined as comprising a straight or branched chain hydrocarbon of between 1 and 20 atoms, which can be saturated or unsaturated, and may include heteroatoms such as nitrogen, sulfur, and oxygen;

"$C_x$-$C_y$ alkylene" means a bridging moiety formed of as few as "x" and as many as "y" —$CH_2$— groups. In the present invention, the term "alkylene" is defined as comprising a bridging hydrocarbon having from 1 to 6 total carbon atoms which is bonded at its terminal carbons to two other atoms (—$CH_2$—)$_x$ where x is 1 to 6;

"$C_x$-$C_y$ alkenyl or alkynyl" means a straight or branched chain hydrocarbon with at least one double bond (alkenyl) or triple bond (alkynyl) between two of the carbon atoms;

"$C_x$-$C_y$ alkoxy" means a straight or branched hydrocarbon chain with as few as x and as many as y carbon atoms, with the chain bonded to the scaffold through an oxygen atom;

"Alkoxycarbonyl" (aryloxycarbonyl) means an alkoxy (aryloxy) moiety bonded to the scaffold through a carbonyl;

"Halogen" or "Halo" means chloro, fluoro, bromo or iodo;

"Acyl" means —C(O)—R, where R is hydrogen, $C_x$-$C_y$ alkyl, aryl, $C_x$-$C_y$ alkenyl, $C_x$-$C_y$ alkynyl, and the like;

"Acyloxy" means —O—C(O)—R, where R is hydrogen, $C_x$-$C_y$ alkyl, aryl, and the like;

"$C_x$-$C_y$ Cycloalkyl" means a hydrocarbon ring or ring system consisting of one or more rings, fused or unfused, wherein at least one of the ring bonds is completely saturated, with the ring(s) having from x to y total carbon atoms;

"Aryl" generally means an aromatic ring or ring system consisting of one or more rings, preferably one to three rings, fused or unfused, with the ring atoms consisting entirely of carbon atoms. In the present invention, the term "aryl" is defined as comprising as an aromatic ring system, either fused or unfused, preferably from one to three total rings, with the ring elements consisting entirely of 5-8 carbon atoms;

"Arylalkyl" means an aryl moiety as defined above, bonded to the scaffold through an alkyl moiety (the attachment chain);

"Arylalkenyl" and "Arylalkynyl" mean the same as "Arylalkyl", but including one or more double or triple bonds in the attachment chain;

"Amine" means a class of organic analogs of nitrogen that may be considered as derived from ammonia ($NH_3$) by replacing one or more of the hydrogen atoms with alkyl groups. The amine is primary, secondary or tertiary, depending upon whether one, two or three of the hydrogen atoms are replaced. A "short chain amine" is one in which the alkyl group contain from 1 to 10 carbon atoms;

"Ammine" means a coordination analog formed by the union of ammonia with a metallic substance in such a way that the nitrogen atoms are linked directly to the metal. It should be noted the difference from amines, in which the nitrogen is attached directly to the carbon atom;

"Amphipathic" means a molecule possessing a polar, water-soluble group covalently bound to a nonpolar, non-non-water-soluble hydrocarbon chain.

"Azide" means any group of analogs having the characteristic formula R($N_3$)x. R may be almost any metal atom, a hydrogen atom, a halogen atom, the ammonium radical, a complex [Co($NH_3$)$_6$], [Hg(CN)$_2$M] (with M=Cu, Zn, Co, Ni), an organic radical like methyl, phenyl, nitrophenol, dinitrophenol, p-nitrobenzyl, ethyl nitrate, and the like. The azide group possesses a chain structure rather than a ring structure;

"Imine" means a class of nitrogen-containing analogs possessing a carbon-to-nitrogen double bond (i.e., R—CH=NH); and "Heterocycle" means a cyclic moiety of one or more rings, preferably one to three rings, fused or unfused, wherein at least one atom of one of the rings is a non-carbon atom. Preferred heteroatoms include oxygen, nitrogen and sulfur, or any combination of two or more of those atoms. The term "Heterocycle" includes furanyl, pyranyl, thionyl, pyrrolyl, pyrrolidinyl, prolinyl, pyridinyl, pyrazolyl, imidazolyl, triazolyl, tetrazolyl, oxathiazolyl, dithiolyl, oxazolyl, isoxazolyl, oxadiazolyl, pyridazinyl, pyrimidinyl, pyrazinyl, piperazinyl, oxazinyl, thiazolyl, and the like.

"Substituted" modifies the identified fragments (moieties) by replacing any, some or all of the hydrogen atoms with a moiety (moieties) as identified in the specification. Substitutions for hydrogen atoms to form substituted analogs include halo, alkyl, nitro, amino (also N-substituted, and N,N disubstituted amino), sulfonyl, hydroxy, alkoxy, phenyl, phenoxy, benzyl, benzoxy, benzoyl, and trifluoromethyl.

The term "Highly Lipophilic Camptothecin Derivatives (HLCDs)", as utilized herein, are defined as camptothecin analogs having a water solubility of less than 5 μg/mL of water.

The terms, "camptothecin analogs" or "Karenitecin® analogs", as utilized herein, refer to camptothecin analogs wherein various types of covalent linkages will connect the substituent group to a silicon or germanium-containing side-chain bound to C7 on the B-ring of said camptothecin analog or Karenitecin® analog, as well as pharmaceutically-acceptable salts, prodrugs, conjugates, hydrates, solvates, polymorphs, and/or tautomeric forms thereof. The silicon atom may also be replaced by germanium.

As utilized herein, the term "pharmaceutically acceptable carriers" refers to carriers useful with the compounds described herein, and are conventional. See, e.g., *Remington's Pharmaceutical Sciences*, by E. W. Martin, Mack Publishing Co., Easton, Pa., 15th Edition (1975), which describes compositions and formulations suitable for pharmaceutical delivery. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As utilized herein, the term "pharmaceutically acceptable salts" includes salts of the active compounds of the present invention which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included, are salts of amino acids such as arginate and the like, and salts of organic acids like glucuronic or galactunoric acids and the like (see, e.g., Berge, et al., Pharmaceutical Salts. *J. Pharm. Sci.* 66:1-19 (1997)). Certain specific compounds of the present invention contain both basic and acidic functionalities that allow the compounds to be converted into either base or acid addition salts.

As utilized herein the term "cancer" refers to all known forms of cancer including, solid forms of cancer (e.g., tumors), lymphomas, and leukemias.

As used herein "anti-neoplastic agent" or "anti-cancer" or "chemotherapeutic agent" or "chemotherapy agent" refer to an agent that reduces, prevents, mitigates, limits, and/or delays the deleterious physiological manifestations, the growth or metastases of neoplasms, or by killing neoplastic cells directly by necrosis or apoptosis of neoplasms or any other mechanism. Chemotherapeutic agents include, for example, fluropyrimidine; pyrimidine nucleosides; purine nucleosides; anti-folates, platinum analogs; anthracycline/anthracenedione; epipodopodophyllotoxin; camptothecin; hormones; hormonal analogs; antihormonals; enzymes, proteins, and antibodies; vinca alkaloids; taxanes; antimicrotubule agents; alkylating agents; antimetabolites; topoisomerase inhibitors; antivirals; and miscellaneous cytostatic agents. "Chemotherapy" refers to treatments using recognized chemotherapeutic agents or chemotherapy agents.

As used herein, an "effective amount" or a "pharmaceutically-effective amount" in reference to the compounds or compositions of the instant invention refers to the amount sufficient to induce a desired biological, pharmacological, or therapeutic outcome in a subject with neoplastic disease. That result can be reduction, prevention, mitigation, delay, shortening the time to resolution of, alleviation of the signs or symptoms of, or exert a medically-beneficial effect upon the underlying pathophysiology or pathogenesis of an expected or observed side-effect, toxicity, disorder or condition, or any other desired alteration of a biological system. In the present invention, the result will generally include the reduction, prevention, mitigation, delay in the onset of, attenuation of the severity of, and/or a hastening in the resolution of, or reversal of chemotherapy-associated toxicity; an increase in the frequency and/or number of treatments; and/or an increase in duration of chemotherapeutic therapy.

As used herein "adverse symptom" means a manifestation or condition that is reported by the patient (e.g., pain, nausea, chills, depression, numbness, tingling, anorexia, dysguesia, and the like); whereas an "adverse sign" means an objective finding that is a physically observable manifestation of a condition, adverse event or disease in the patient (e.g., palpable purpura, maculopapular rash, spider angioma, Chvostek's sign, Babinski's sign, Trousseau's sign, opisthotonos, and the like).

Unless otherwise explained, all technical and scientific terms used herein have the same meaning as commonly understood by one of ordinary skill in the art to which this disclosure belongs. Although methods and materials similar or equivalent to those described herein can be used in the practice or the disclosed methods and compositions, suitable methods and materials are described below. All publications, patent applications, patents, and other references mentioned herein are incorporated by reference in their entirety. In case of conflict, the present Specification, including explanations of terms, will control. In addition, the materials, methods, and examples are for illustrative purposes only, and are not intended to be limiting.

I. Karenitecin®/BNP1350

Highly lipophilic camptothecin derivatives (HLCDs), particularly those containing silicon-based moieties, are effective anticancer drugs. One of the most noted of the silicon-containing HLCDs is Karenitecin® (also known as BNP1350; IUPAC Nomenclature: (4S)-4-ethyl-4-hydroxy-11-[2-(trimethylsilyl)ethyl]-1H-pyrano[3':4':6,7]indolizino[1,2-b]quinoline-3,14(4H,12H)-dione, and also referred to as 7-(2'-trimethylsilyl)ethyl camptothecin)), currently in human clinical trials in the United States and internationally. U.S. Pat. Nos. 5,910,491 and 6,194,579; and U.S. patent application Ser. No. 10/627,444, filed Jul. 25, 2003, which are incorporated by reference herein in their entirety, describe the compositions, formulations, and processes for making Karenitecin® and other related HLCDs.

Highly lipophilic camptothecin derivatives (HLCDs), particularly those containing silicon-based moieties, are effective anti-cancer drugs. One of the most noted of the silicon-containing HLCDs is Karenitecin® (also known as BNP1350; IUPAC Nomenclature: (4S)-4-ethyl-4-hydroxy-11-[2-(trimethylsilyl)ethyl]-1H-pyrano[3':4':6,7]indolizino[1,2-b]quinoline-3,14(4H,12H)-dione and also referred to as 7-(2'-trimethylsilyl)ethyl camptothecin), currently in human clinical trials in the United States and internationally. U.S. Pat. Nos. 5,910,491 and 6,194,579; and U.S. patent application Ser. No. 10/627,444, filed Jul. 25, 2003, which are incorporated by reference herein in their entirety, describe the compositions, formulations, and processes for making Karenitecin® and other related HLCDs.

The Karenitecin® analogs disclosed and claimed in the present invention represent a novel class of chemotherapeutic compounds that have exhibited potent antineoplastic activity against common types of cancer including but not limited to cancers of the lung, breast, prostate, pancreas, head and neck, ovary, colon, as well as melanoma. While these Karenitecin® analogs possess Topoisomerase I inhibitory activity similar to that of other camptothecin derivatives, they also possess novel structural modifications that are rationally designed for superior bioavailability and tissue penetration, while concomitantly avoiding untoward metabolism and drug resistance mechanisms which are common in human and other mammalian cancers.

The present invention discloses, in a non-limiting manner, analogs of the anti-tumor agent Karenitecin® wherein various types of covalent linkages will connect the novel side chain at the C10 position on the A-ring of the Karenitecin® molecule. However, it should be noted that the silicon of Karenitecin® may also be substituted with germanium. These analogs are amphipathic and exploit the polar side chains to decrease protein binding and to augment intracellular uptake and tissue retention. The polar group on the side chain of these Karenitecin® analogs will reduce drug-binding affinity to plasma proteins, so as to improve plasma protein binding properties while concomitantly maintaining both lactone stability and drug potency. The increased free (i.e., non-plasma protein bound) drug in human plasma will improve the bioavailability of the parent compound. Moreover, as previously discussed, the hydrolysis of the lactone E-ring of the camptothecin molecule (thus forming the water soluble carboxylate form) only possesses approximately one-tenth or less of the anti-tumor potency of the original, non-hydrolyzed closed lactone E-ring form of the camptothecin molecule.

It may be ascertained from the pharmacological and biochemical data presented in Section IV, in THE BACKGROUND OF THE INVENTION section, that many of the previously synthesized camptothecin analogs possess a number of inherent limitations which markedly decreases their usefulness as anti-cancer agents. In contrast, Karenitecin® is a highly lipophilic camptothecin derivative characterized by substantial lactone stability and long plasma half-life. In vitro studies conducted on a panel of over 20 human cancer cell lines indicate that Karenitecine® is significantly more potent antitumor agent than either Topotecan™ or SN-38, the active metabolite of Irinotecan™. Equilibrium dialysis studies with human plasma demonstrated that Karenitecin® is 98 to 99% protein-bound. The free drug concentration in blood plasma is generally considered to be the pharmacologically active form in clinical pharmacology.

In addition, the analogs of the present invention have significant utility as highly efficacious chemotherapeutic drugs, and are significantly less toxic than previously disclosed camptothecin derivatives. These novel analogs may also not undergo A-ring or B-ring glucuronidation (and implicitly deglucuronidation) similar to the parent Karenitecin® molecule. The lack of glucuronidation decreases deleterious physiological side-effects (e.g., diarrhea, leukopenia) and may also mitigate substantial interpatient variability in drug levels of the free metabolite and its glucuronide conjugate. Furthermore, these novel analogs are not prodrugs, requiring metabolic activation.

Thus, in summation, the novel Karenitecin® analogs of the present invention: (i) possess potent antitumor activity (i.e., in nanomolar or subnanomolar concentrations) for inhibiting the growth of human and animal tumor cells in vitro; (ii) are potent inhibition of Topoisomerase I; (iii) lack of susceptibility to MDR/MRP drug resistance; (iv) require no metabolic drug activation: (v) lack glucuronidation of the A-ring or B-ring; (vi) possess a low molecular weight (e.g., MW<600); and (vii) are highly soluble in organic pharmaceutical solvents or co-solvents (e.g., propylene glycol, PEG 300-400, dimethyl acetamide, dimethyl isosorbide, n-methyl pyrrolidinone).

The novel Karenitecin® analogs disclosed and claimed in the present invention possess the generic structural formula illustrated, below.

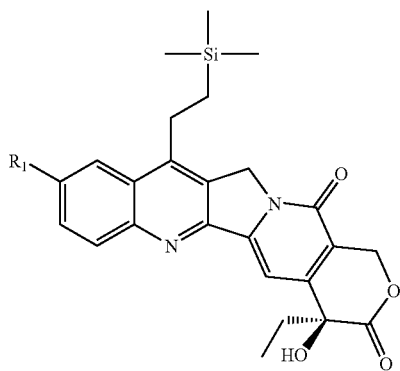

wherein:

$R_1$=short alkyl chain or alkyl chain containing polar functional groups attached to C10 of the A-ring of Karenitecin®.

I. Synthesis of Karenitecin® Analogs

1. Preparation of 7-(2'-Trimethylsilanyl)ethyl-10-methoxy camptothecin (Compound 1)

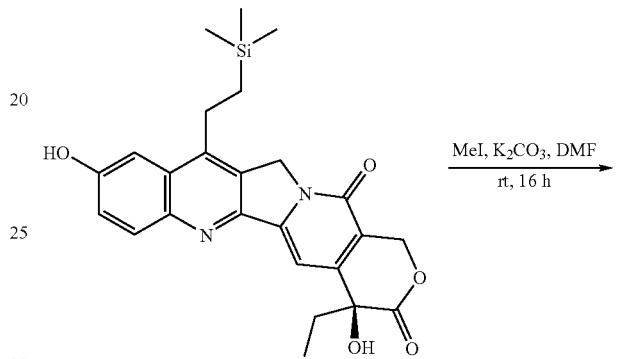

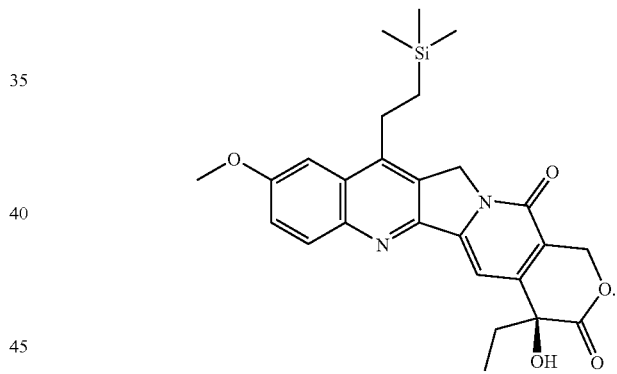

To a solution of 7-(2'-trimethylsilanyl)ethyl-10-hydroxy camptothecin (50 mg, 0.11 mmol) and potassium carbonate (100 mg, 0.72 mmol) in N,N-dimethylformamide (3 mL) was added methyl iodide (0.5 mL). The resulted solution was stirred at room temperature for 16 hours. N,N-Dimethylformamide and excess methyl iodide were removed by evaporation under reduced pressure. The residue was filtrated through silica gel with methanol/dichloromethane (10/90) and concentrated by rotary evaporation. Purification by radial preparative-layer chromatography (dichloromethane) provided 45 mg of Compound 1 as a yellow solid:

$^1$H NMR (300 MHz, CDCl$_3$) δ 8.06 (d, 1H, J=9.3 Hz), 7.54 (s, 1H), 7.39 (dd, 1H, J$_1$=9.3 Hz, J$_2$=2.7 Hz), 7.16 (s, 1H), 5.69 (d, 1H, J=16.2 Hz), 5.24 (d, 1H, J=16.2 Hz), 5.16 (s, 2H), 3.92 (s, 3H), 3.02-2.96 (m, 2H), 1.90-1.76 (m, 2H), 0.97 (t, 3H, J=7.2 Hz, 0.89-0.84 (m, 2H), 0.12 (s, 9H).

MS (m/z, M+1) 479.6

2. Preparation of 7-(2'-Trimethylsilanyl)ethyl-10-methoxymethoxy camptothecin (Compound 2)

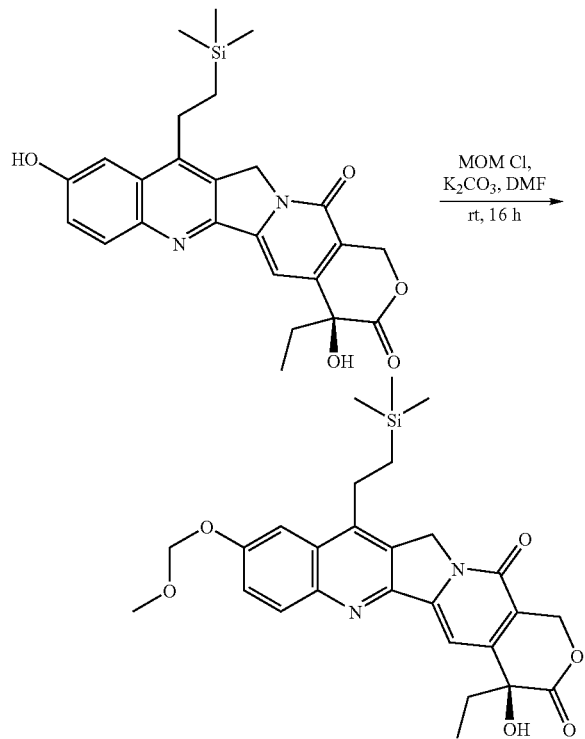

To a solution of 7-(2'-trimethylsilanyl)ethyl-10-hydroxy camptothecin (41 mg, 0.088 mmol) and potassium carbonate (15 mg, 0.11 mmol) in N,N-dimethylformamide (2 mL) was added methoxymethyl chloride (0.03 ml) at −78° C. The resultant solution was stirred at room temperature for 16 hours. N,N-Dimethylformamide and excess methoxymethyl chloride were removed by evaporation under reduced pressure. The residue was filtrated through silica gel with methanol/dichloromethane (10/90) and concentrated by rotary evaporation. Purification by radial preparative-layer chromatography (ethyl acetate/hexanes 50/50 to methanol/chloroform 2/98) provided 20 mg of Compound 2 as a yellow solid.

$^1$H NMR (300 MHz, DMSO) δ 8.11 (d, 1H, J=9.9 Hz), 7.60-7.57 (m, 2H), 7.28 (s, 1H), 6.51 (s, 1H), 5.43 (s, 2H), 5.41 (s, 2H), 5.30 (s, 2H), 3.46 (s, 3H), 3.10-3.02 (m, 2H), 1.95-1.78 (m, 2H), 0.95-0.86 (m, 5H), 0.16 (s, 9H).

MS (m/z, M+1) 509.6

3. Preparation of 7-(2'-Trimethylsilanyl)ethyl-10-(3'-hydroxypropoxy) camptothecin (Compound 3)

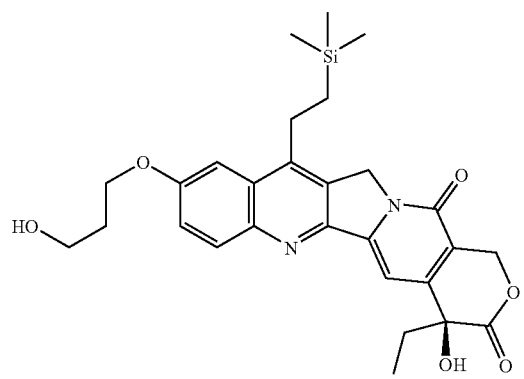

To a solution of 7-(2'-trimethylsilanyl)ethyl-10-hydroxy camptothecin (31 mg, 0.067 mmol) and potassium carbonate (15 mg, 0.11 mmol) in N,N-dimethylformamide (2 mL) was added 3-iodopropanol (0.1 ml) at −78° C. The resultant solution was stirred at room temperature for 16 hours. N,N-Dimethylformamide was removed by evaporation under reduced pressure. The residue was filtrated through silica gel with methanol/dichloromethane (10/90) and concentrated by rotary evaporation. Purification by radial preparative-layer chromatography (ethyl acetate/hexanes 50/50 to methanol/chloroform 2/98) provided 15 mg of 7-(2'-trimethylsilanyl)ethyl-10-(3'-hydroxypropoxy) camptothecin (Compound 3) as a yellow solid.

$^1$H NMR (300 MHz, CDCl$_3$) δ 8.02 (d, 1H, J=9.3 Hz), 7.52 (s, 1H), 7.34 (dd, 1H, J$_1$=9.3 Hz, J$_2$=2.7 Hz), 7.14 (d, 1H, J=2.7 Hz), 5.67 (d, 1H, J=16.5 Hz), 5.22 (d, 1H, J=16.5 Hz), 5.09 (s, 2H), 4.24-4.17 (m, 2H), 3.90-3.85 (m, 2H), 3.00-2.88 (m, 2H), 2.12-2.06 (m, 2H), 1.90-1.76 (m, 2H), 0.97 (t, 3H, J=7.3 Hz), 0.86-0.80 (m, 2H), 0.11 (s, 9H).

MS (m/z, M+1) 523.6

4. Preparation of 7-(2'-Trimethylsilanyl)ethyl-10-(2'-methoxyethoxy)camptothecin (Compound 4)

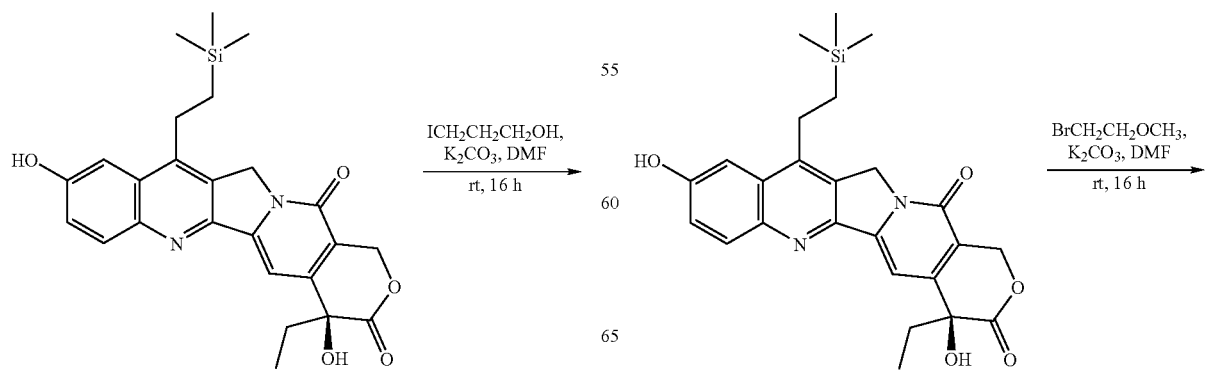

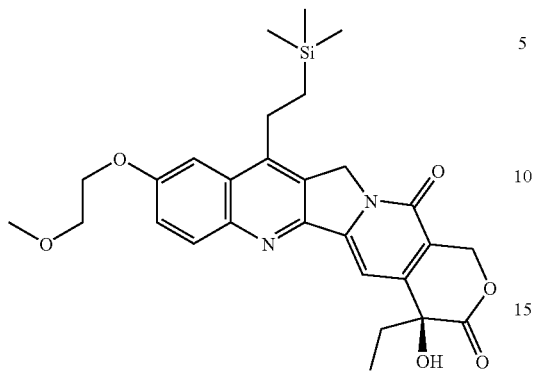

To a solution of 7-(2'-trimethylsilanyl)ethyl-10-hydroxy camptothecin (31 mg, 0.067 mmol) and potassium carbonate (11 mg, 0.08 mmol) in N,N-dimethylformamide (2 mL) was added methoxyethyl bromide (0.1 ml) at −78° C. The resultant solution was stirred at room temperature for 16 hours. N,N-Dimethylformamide and excess methoxyethyl bromide were removed by evaporation under reduced pressure. The residue was filtrated through silica gel with methanol/dichloromethane (10/90) and concentrated by rotary evaporation. Purification by radial preparative-layer chromatography (ethyl acetate/hexanes 50/50 to methanol/chloroform 2/98) provided 15 mg of 7-(2'-trimethylsilanyl)ethyl-10-(2'-methoxyethoxy) camptothecin (Compound 4) as a yellow solid.

$^1$H NMR (300 MHz, CDCl$_3$) δ 8.06 (d, 1H, J=9.3 Hz), 7.53 (s, 1H), 7.43 (dd, 1H, J$_1$=9.3 Hz, J$_2$=2.7 Hz), 7.21 (s, 1H), 5.69 (d, 1H, J=16.2 Hz), 5.24 (d, 1H, J=16.2 Hz), 5.15 (s, 2H), 4.24-4.20 (m, 2H), 3.82-3.79 (m, 2H), 3.69 (s, 1H), 3.44 (s, 3H), 3.00-2.94 (m, 2H), 1.90-1.76 (m, 2H), 0.97 (t, 3H, J=7.2 Hz), 0.88-0.82 (m, 2H), 0.12 (s, 9H).

MS (m/z, M+1) 523.7

5. Preparation of 7-(2'-Trimethylsilanyl)ethyl-10-isopropoxy camptothecin (Compound 5)

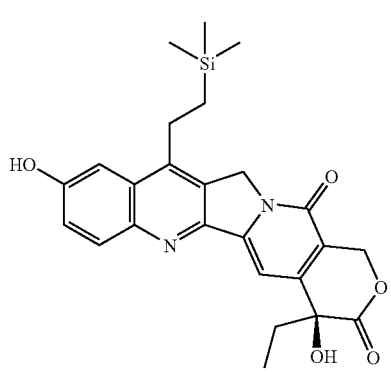

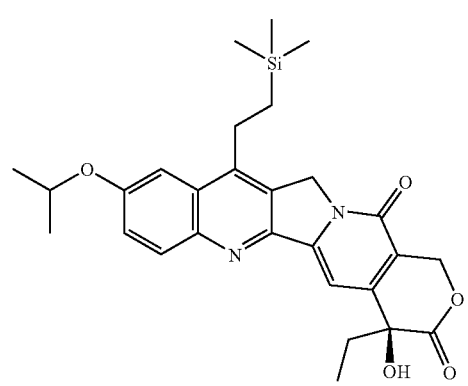

To a solution of 7-(2'-trimethylsilanyl)ethyl-10-hydroxy camptothecin (27 mg, 0.058 mmol) and potassium carbonate (88 mg, 0.64 mmol) in N,N-dimethylformamide (1 mL) was added isopropyl iodide (0.05 ml). The resultant solution was stirred at room temperature for 16 hours. N,N-Dimethylformamide and excess isopropyl iodide were removed by evaporation under reduced pressure. The residue was filtrated through silica gel with methanol/dichloromethane (10/90) and concentrated by rotary evaporation. Purification by radial preparative-layer chromatography (ethyl acetate/hexanes 10/90 to 50/50) provided 20 mg of 7-(2'-trimethylsilanyl) ethyl-10-isopropoxy camptothecin (Compound 5) as a yellow solid.

$^1$H NMR (300 MHz, CDCl$_3$) δ 8.05 (d, 1H, J=9.3 Hz), 7.53 (s, 1H), 7.36 (dd, 1H, J$_1$=9.2 Hz, J$_2$=2.7 Hz), 7.18 (d, 1H, J=3.3 Hz), 5.71 (d, 1H, J=16.5 Hz), 5.25 (d, 1H, J=16.5 Hz), 5.16 (s, 2H), 4.72-4.64 (m, 1H), 3.62 (s, 1H), 3.02-2.94 (m, 2H), 1.88-1.77 (m, 2H), 1.40 (d, 6H, J=6.0 Hz), 0.98 (t, 3H, J=7.2 Hz), 0.89-0.83 (m, 2H), 0.12 (s, 9H).

MS (m/z, M+1) 507.7

6. Preparation of 5-Hydroxy-7-(2'-trimethylsilanyl) ethyl-10-ethoxy camptothecin (Compound 6)

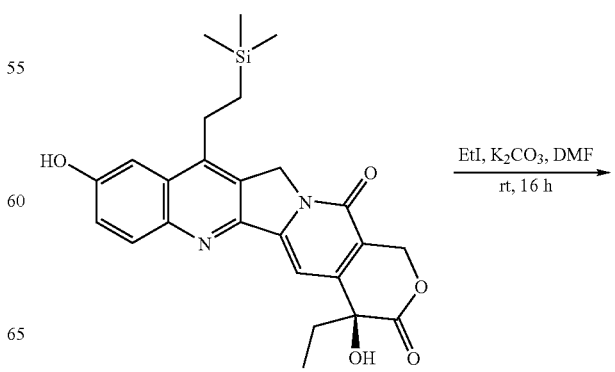

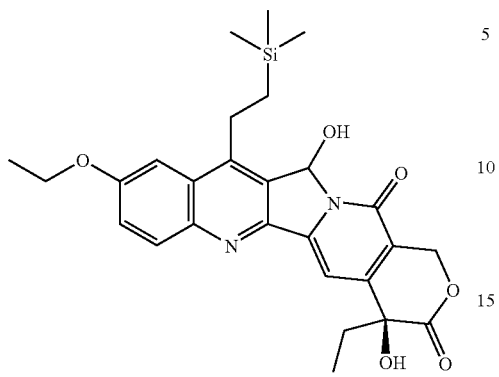

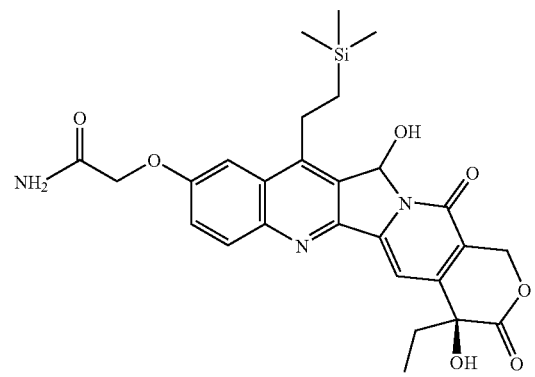

To a solution of 7-(2'-trimethylsilanyl)ethyl-10-hydroxy camptothecin (40 mg, 0.086 mmol) and potassium carbonate (18 mg, 0.13 mmol) in N,N-dimethylformamide (2 mL) was added ethyl iodide (0.1 ml) at −78° C. The resultant solution was stirred at room temperature for 16 hours. N,N-Dimethylformamide and excess ethyl iodide were removed by evaporation under reduced pressure. The residue was filtrated through silica gel with methanol/dichloromethane (10/90) and concentrated by rotary evaporation. Purification by radial preparative-layer chromatography (ethyl acetate/hexanes 10/90 to 50/50) provided 10 mg of 5-hydroxy-7-(2'-trimethylsilanyl)ethyl-10-ethoxy camptothecin (Compound 6) as a yellow solid.

$^1$H NMR (300 MHz, CDCl$_3$) δ 7.99 (dd, 1H, J$_1$=9.3 Hz, J$_2$=12.0 Hz), 7.43 (d, 1H, J=12.9 Hz), 7.38-7.31 (m, 1H), 7.15 (t, 1H, J=1.8 Hz), 6.97 (dd, 1H, J$_1$=3.3 Hz, J$_2$=7.8 Hz), 5.60 (d, 1H, J=16.2 Hz), 5.33-5.11 (m, 2H), 4.15-4.09 (m, 2H), 3.87 (s, 1H), 3.18-2.98 (m, 2H), 1.86-1.77 (m, 2H), 1.47 (t, 3H, J=6.9 Hz), 1.02-0.87 (m, 5H), 0.11 (s, 9H).

MS (m/z, M+1) 509.6

7. Preparation of 5-Hydroxy-7-(2'-trimethylsilanyl)ethyl-10-amidomethoxy camptothecin (Compound 7)

To a solution of 7-(2'-trimethylsilanyl)ethyl-10-hydroxy camptothecin (52 mg, 0.11 mmol) and potassium carbonate (27 mg, 0.20 mmol) in N,N-dimethylformamide (1 mL) was added iodoacetamide (25 mg, 0.1352 mmol) at −78° C. The resultant solution was stirred at room temperature for 16 hours. N,N-Dimethylformamide was removed by vacuum. The residue was filtrated through silica gel with methanol/dichloromethane (10/90) and concentrated by rotary evaporation. Purification by radial preparative-layer chromatography (ethyl acetate/hexanes 10/90 to 50/50) provided 12 mg of 5-hydroxy-7-(2'-trimethylsilanyl)ethyl-10-amidomethoxy camptothecin (Compound 7) as a yellow solid.

$^1$H NMR (300 MHz, DMSO) δ 8.07 (d, 1H, J=9.6 Hz), 7.70 (s, 1H), 7.60-7.54 (m, 2H), 7.50 (s, 1H), 7.30 (d, 1H, J=2.7 Hz), 7.12 (d, 1H, J=7.5 Hz), 6.97 (dd, 1H, J$_1$=8.4 Hz, J$_2$=15.6 Hz), 6.50 (d, 1H, J=5.4 Hz), 5.39 (d, 2H, J=6.0 Hz), 4.64 (s, 2H), 3.20-2.99 (m, 2 H), 1.92-1.78 (m, 2H), 0.97-0.85 (m, 5H), 0.16 (s, 9H).

MS (m/z, M+1) 538.5

8. Preparation of 7-(2'-Trimethylsilanyl)ethyl-10-(dimethylcarbamoyloxy) camptothecin (Compound 8)

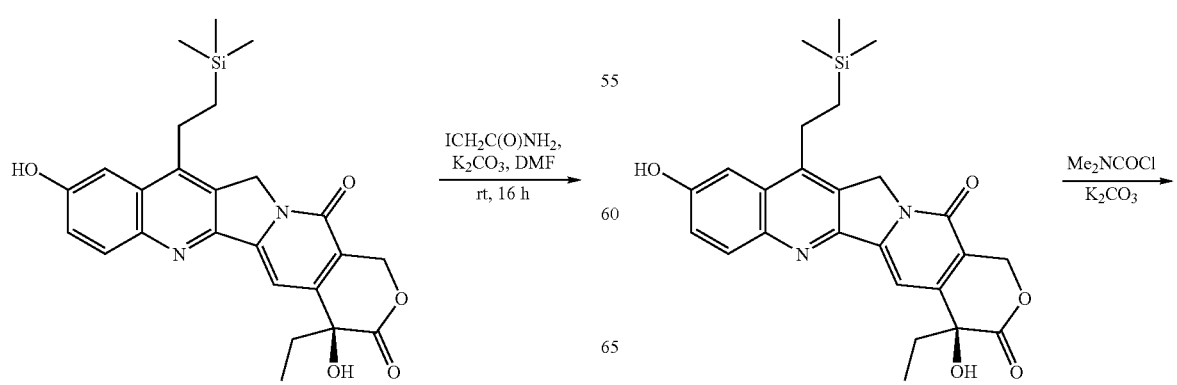

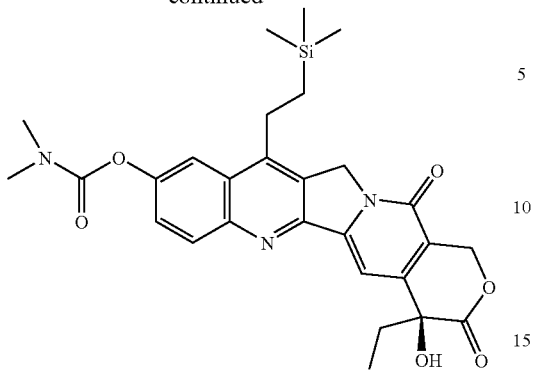

To a solution of 7-(2'-trimethylsilanyl)ethyl-10-hydroxy camptothecin (29 mg, 0.062 mmol) and potassium carbonate (19 mg, 0.14 mmol) in N,N-dimethylformamide (1 mL) was added a solution of dimethylcarbamyl chloride (9 mg, 0.08115 mmol) in dimethoxyethane (0.8 ml) at −78° C. The resultant solution was stirred at room temperature for 16 hours. The reaction was quenched with 1 N HCl and extracted with dichloromethane. The organic combinations was filtrated through silica gel with methanol/dichloromethane (10/90) and concentrated by rotary evaporation. Purification by radial preparative-layer chromatography (ethyl acetate/hexanes 10/90 to 50/50) provided 22 mg of 7-(2'-trimethylsilanyl)ethyl-10-(dimethylcarbamoyloxy)camptothecin (Compound 8) as a yellow solid.

$^1$H NMR (300 MHz, CDCl$_3$) δ 8.14 (d, 1H, J=9.0 Hz), 7.65 (d, 1H, J=2.4 Hz), 7.60 (s, 1 H), 7.53 (dd, 1H, J$_1$=9.0 Hz, J$_2$=2.7 Hz), 5.68 (d, 1H, J=16.5 Hz), 5.24 (d, 1H, J=16.5 Hz), 5.15 (s, 2H), 3.83 (s, 1H), 3.13 (s, 3H), 3.01 (s, 3H), 3.01-2.94 (m, 2H), 1.90-1.73 (m, 2H), 0.96 (t, 3H, J=7.5 Hz), 0.87-0.82 (m, 2H), 0.11 (s, 9H).

MS (m/z, M+1) 536.6

9. Preparation of 7-(2'-Trimethylsilanyl)ethyl-10-(ethoxycarbonylmethoxy) camptothecin (Compound 9)

To a solution of 7-(2'-trimethylsilanyl)ethyl-10-hydroxy camptothecin (35 mg, 0.075 mmol) and potassium bicarbonate (15 mg, 0.15 mmol) in N,N-dimethylformamide (1 mL) was added ethyl iodoacetate (0.2 mL). The resultant solution was stirred at room temperature for 3 days. The reaction was quenched with acetic acid (0.2 mL). N,N-dimethylformamide was removed by vacuum. The residue was filtrated through silica gel with methanol/dichloromethane (10/90) and concentrated by rotary evaporation. Purification by radial preparative-layer chromatography (ethyl acetate/hexanes 10/90 to 50/50) provided the ester Compound 9 as a yellow solid.

$^1$H NMR (300 MHz, CDCl$_3$) δ 8.10 (d, 1H, J=9.0 Hz), 7.55 (s, 1H), 7.44 (dd, 1H, J$_1$=9.3 Hz, J$_2$=2.7 Hz), 7.16 (d, 1H, J=2.7 Hz), 5.68 (d, 1H, J=16.2 Hz), 5.24 (d, 1H, J=16.2 Hz), 5.14 (s, 2H), 4.73 (s, 2H), 4.24 (dd, 2H, J$_1$=14.3 Hz, J$_2$=6.9 Hz), 3.01-2.94 (m, 2H), 1.90-1.73 (m, 2H), 1.25 (t, 3H, J=7.2 Hz), 0.96 (t, 3H, J=7.5 Hz), 0.87-0.79 (m, 2H), 0.12 (s, 9H).

MS (m/z, M+1) 551.7

10. Preparation 7-(2'-Trimethylsilanyl)ethyl-10-(amidomethyloxy)camptothecin (Compound 10)

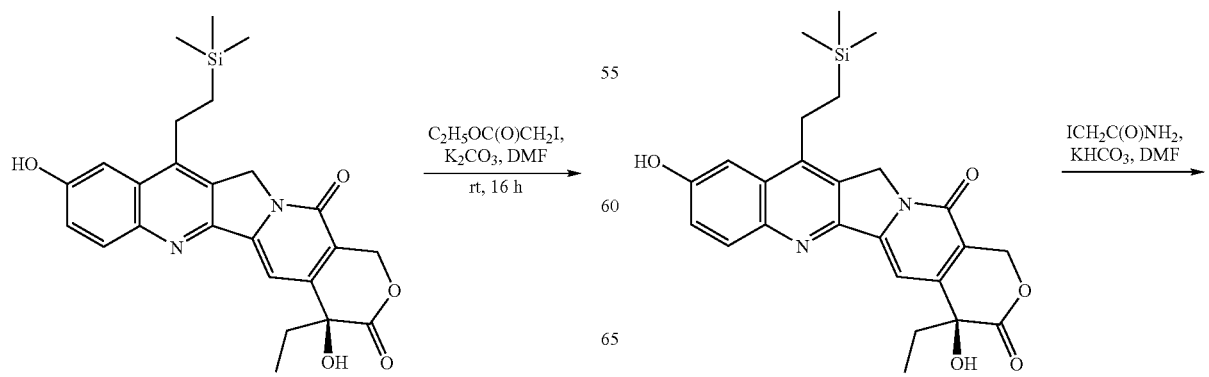

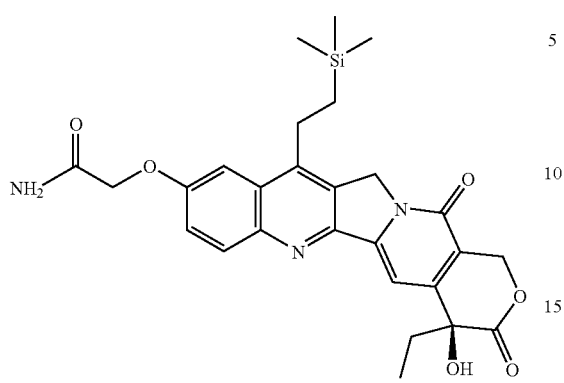

To a solution of 7-(2'-trimethylsilanyl)ethyl-10-hydroxy camptothecin (35 mg, 0.075 mmol) and potassium bicarbonate (11 mg, 0.11 mmol) in N,N-dimethylformamide (1.5 mL) was added iodoacetamide (21 mg, 0.11 mmol). The resultant solution was stirred at 50° C. for 4 hours. The reaction was quenched with 1 N HCl and extracted with dichloromethane. The organic combinations were filtrated through silica gel with methanol/dichloromethane (10/90) and concentrated by rotary evaporation. Purification by radial preparative-layer chromatography (methanol/dichloromethane 2/98) provided 20 mg of the amide Compound 10 as a yellow solid.

$^1$H NMR (300 MHz, CDCl$_3$) δ 8.12 (d, 1H, J=9.3 Hz), 7.55 (s, 1H), 7.43 (dd, 1H, J$_1$=9.3 Hz, J$_2$=2.7 Hz), 7.22 (d, 1H, J=2.7 Hz), 5.69 (d, 1H, J=16.2 Hz), 5.24 (d, 1H, J=16.2 Hz), 5.16 (s, 2H), 4.61 (s, 2H), 3.71 (s, 1H), 3.01-2.96 (m, 2H), 1.90-1.75 (m, 2H), 0.98 (t, 3H, J=7.5 Hz), 0.88-0.81 (m, 2H), 0.13 (s, 9H).

MS (m/z, M+1) 522.6

11. Preparation of 7-(2'-Trimethylsilanyl)ethyl-10-(carboxymethyloxy) camptothecin (Compound 11)

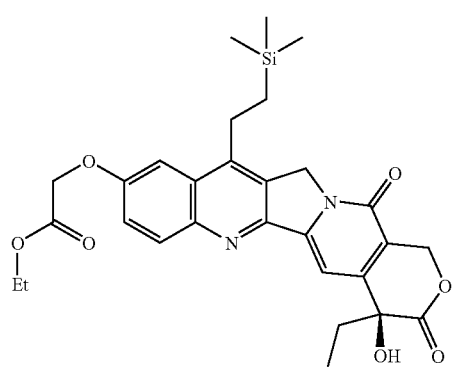

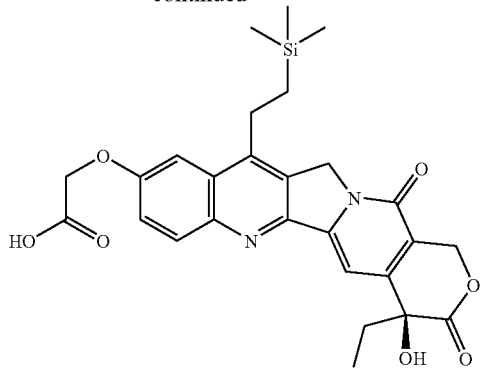

To a solution of 7-(2'-trimethylsilanyl)ethyl-10-(ethoxycarbonylmethyl)oxy camptothecin (Compound 6; 35 mg, 0.064 mmol) in ethanol (2 mL) was added a solution of potassium carbonate (44 mg, 0.32 mmol) in water (2 mL). The resultant mixture was stirred at room temperature for four hours. The reaction was quenched with 1 N HCl (2 mL) and extracted with dichloromethane. The organic combinations was filtrated through silica gel with methanol/dichloromethane (10/90) and concentrated by rotary evaporation. Purification by radial preparative-layer chromatography (methanol/dichloromethane 2/98) provided the acid Compound 11 as a yellow solid.

MS (m/z, M+1) 523.7

12. Preparation of 7-(2'-Trimethylsilanyl)ethyl-10-(4-morpholinecarbonyloxy) camptothecin (Compound 12)

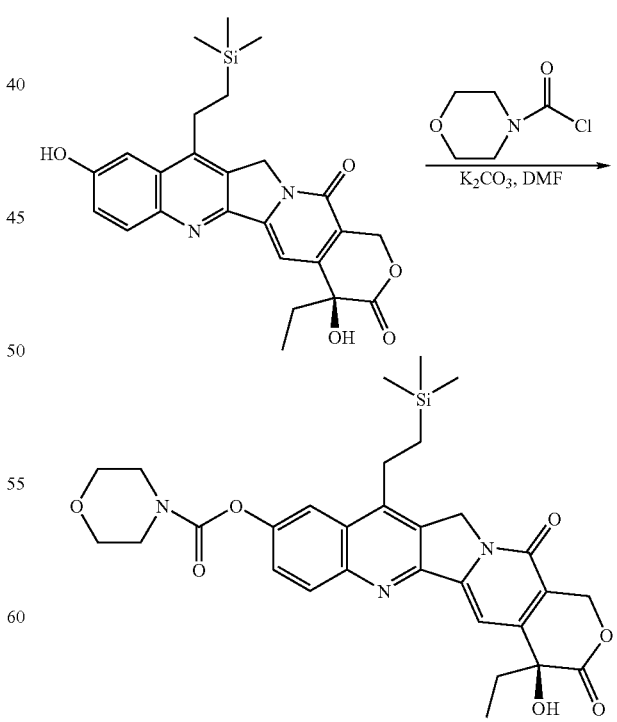

To a solution of 7-(2'-trimethylsilanyl)ethyl-10-hydroxy camptothecin (41 mg, 0.088 mmol) and potassium carbonate (18 mg, 0.13 mmol) in N,N-dimethylformamide (2 mL) was added 4-morphlinecarbonyl chloride (0.15 mL). The resultant solution was stirred at room temperature for 16 hours. The reaction was quenched with water and extracted with dichloromethane (4×3 mL). The organic combinations were filtrated through silica gel with 10% methanol/dichloromethane and concentrated by rotary evaporation. Purification by radial preparative-layer chromatography (ethyl acetate/hexanes 10/90 to 50/50) provided Compound 12 as a yellow solid.

$^1$H NMR (300 MHz, CDCl$_3$) δ 8.16 (d, 1H, J=9.0 Hz), 7.67 (d, 1H, J=2.4 Hz), 7.58 (s, 1 H), 7.52 (dd, 1H, J$_1$=9.0 Hz, J$_2$=2.4 Hz), 5.68 (d, 1H, J=16.5 Hz), 5.24 (d, 1H, J=16.5 Hz), 5.16 (s, 2H), 3.82 (s, 1H), 3.75-3.57 (m, 8H), 3.01-2.94 (m, 2H), 1.90-1.73 (m, 2H), 0.96 (t, 3H, J=7.5 Hz), 0.88-0.83 (m, 2H), 0.11 (s, 9H).

MS (m/z, M+1) 578.7

13. Preparation of 7-(2'-Trimethylsilanyl)ethyl-10-(dimethylthiocarbamoyloxy) camptothecin (Compound 13)

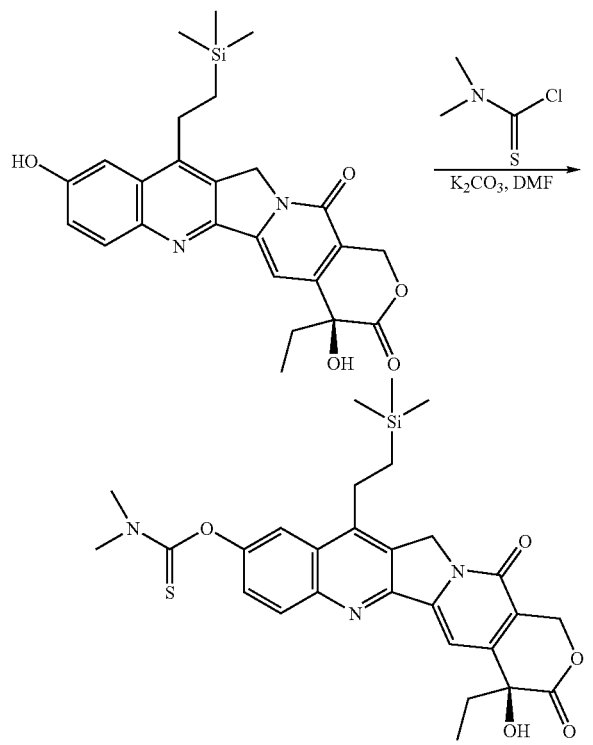

To a solution of 7-(2'-trimethylsilanyl)ethyl-10-hydroxy camptothecin (43 mg, 0.093 mmol) and potassium carbonate (19 mg, 0.14 mmol) in N,N-dimethylformamide (2 mL) was added dimethylthiocarbamoyl chloride (65 mg, 0.53 mmol) at −78° C. The resultant solution was stirred at room temperature for 16 hours and 50° C. for 4 hours. Another portion of dimethylthiocarbamoyl chloride (40 mg, 0.32 mmol), diisopropylethylamine (3 mL) and N,N-dimethylaminopyridine (catalytic amount) were then added. The resultant solution was stirred at room temperature for another 3 days. The reaction was quenched with saturated sodium bicarbonate solution and extracted with chloroform (4×3 mL). The organic combinations were filtrated through silica gel with 10% methanol/dichloromethane and concentrated by rotary evaporation. Purification by radial preparative-layer chromatography (ethyl acetate/hexanes 50/50 to methanol/dichloromethane 2/98) provided 28 mg of Compound 13 as a yellow solid.

$^1$H NMR (300 MHz, CDCl$_3$) δ 8.17 (d, 1H, J=9.3 Hz), 7.60 (s, 2H), 7.49 (dd, 1H, J$_1$=9.2 Hz, J$_2$=2.7 Hz), 5.68 (d, 1H, J=16.5 Hz), 5.24 (d, 1H, J=16.5 Hz), 5.16 (s, 2H), 3.85 (s, 1H), 3.45 (s, 3H), 3.38 (s, 3H), 3.01-2.94 (m, 2H), 1.95-1.76 (m, 2H), 0.97 (t, 3H, J=7.2 Hz), 0.89-0.83 (m, 2H), 0.096 (s, 9H).

MS (m/z, M+1) 552.7

14. Preparation of 7-(2'-Trimethylsilanyl)ethyl-10-ethoxy camptothecin (Compound 14)

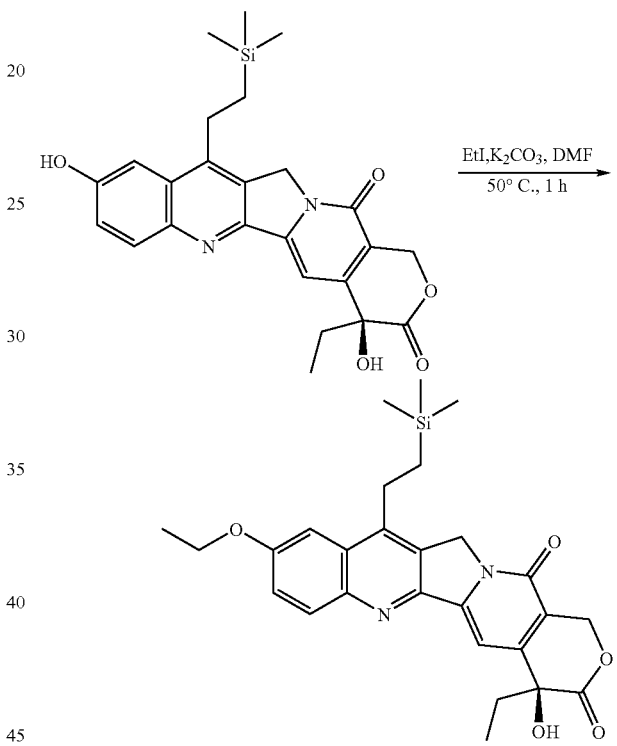

To a solution of 7-(2'-trimethylsilanyl)ethyl-10-hydroxy camptothecin (30 mg, 0.065 mmol) and sodium bicarbonate (9 mg, 0.098 mmol) in N,N-dimethylformamide (1 mL) was added ethyl iodide (0.1 ml). The resultant solution was stirred at 50° C. for 4 hours. Potassium carbonate (10 mg, 0.072 mmol) was added and the mixture was stirred at 50° C. for another 2 hours. N,N-Dimethylformamide and excess ethyl iodide were removed by evaporation under reduced pressure. The residue was filtrated through silica gel with methanol/dichloromethane (10/90) and concentrated by rotary evaporation. Purification by radial, preparative-layer chromatography (methanol/dichloromethane 2/98) provided 7 mg of 7-(2'-trimethylsilanyl)ethyl-10-ethoxy camptothecin (Compound 14) as a yellow solid.

$^1$H NMR (300 MHz, CDCl$_3$) δ 8.12 (d, 1H, J=9.3 Hz), 7.60 (s, 1H), 7.45 (dd, 1H, J$_1$=9.2 Hz, J$_2$=2.4 Hz), 7.22 (d, 1H, J=2.7 Hz), 5.75 (d, 1H, J=16.2 Hz), 5.30 (d, 1H, J=16.2 Hz), 5.22 (s, 2H), 4.20 (dd, 2H, J$_1$=Hz, J$_2$=Hz), 3.71 (s, 1H), 3.08-2.98 (m, 2H), 1.97-1.82 (m, 2 H), 1.54 (t, 3H, J=6.9 Hz), 1.04 (t, 3H, J=7.2 Hz), 0.98-0.88 (m, 2H), 0.18 (s, 9H).

MS (m/z, M+1) 493.6

15. Preparation of 7-(2'-Trimethylsilanyl)ethyl-10-cyanomethoxy camptothecin (Compound 15)

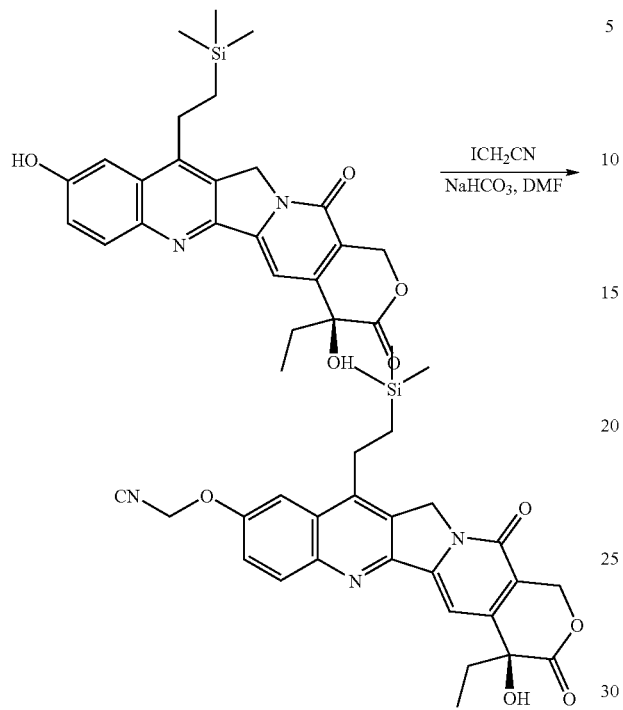

To a solution of 7-(2'-trimethylsilanyl)ethyl-10-hydroxy camptothecin (48 mg, 0.10 mmol) and sodium bicarbonate (14 mg, 0.15 mmol) in N,N-dimethylformamide (2 mL) was added iodoacetonitrile (0.2 mL). The resultant solution was stirred at 50° C. for 4 hours. Sodium bicarbonate (14 mg, 0.15 mmol) and iodoacetonitrile (0.1 mL) were then added. The mixture was stirred at 50° C. for another 2 hours. N,N-Dimethylformamide was removed by evaporation under reduced pressure. The residue was filtrated through silica gel with methanol/dichloromethane (10/90) and concentrated by rotary evaporation. Purification by radial preparative-layer chromatography (methanol/dichloromethane 2/98) provided 20 mg of 7-(2'-trimethylsilanyl)ethyl-10-cyanomethoxy camptothecin (Compound 15) as a yellow solid.

$^1$H NMR (300 MHz, CDCl$_3$) δ 8.20 (d, 1H, J=9.3 Hz), 7.62 (s, 1H) 7.49 (dd, 1H, J$_1$=9.3 Hz, J$_2$=3.0 Hz), 7.40 (d, 1H, J=3.0 Hz), 5.75 (d, 1H, J=16.2 Hz), 5.30 (d, 1H, J=16.2 Hz), 5.24 (s, 2H), 4.95 (s, 2H), 3.81 (s, 1H), 3.13-3.05 (m, 2H), 1.97-1.85 (m, 2H), 1.04-0.92 (m, 5H), 0.21 (s, 9H).

MS (m/z, M+1) 504.6

16. Preparation of 10-(Trimethylsilanylmethoxy)camptothecin (Compound 16)

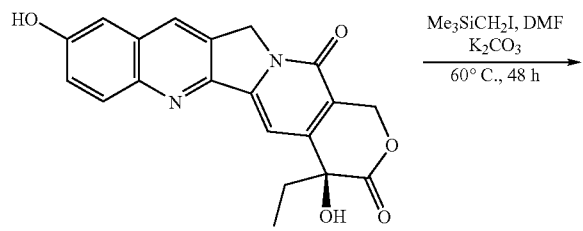

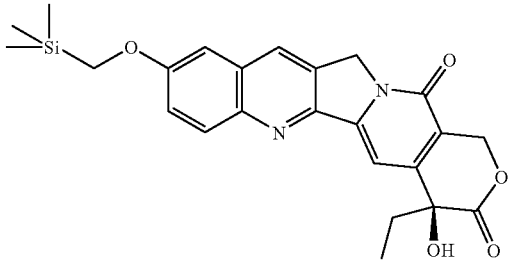

To a solution of 10-hydroxy camptothecin (85 mg, 0.23 mmol) and potassium carbonate (100 mg, 0.72 mmol) in N,N-dimethylformamide (1.7 mL) was added iodomethyltrimethylsilane (0.15 mL). The resultant solution was stirred at 60° C. for 48 hours. The reaction was then quenched with acetic acid (0.2 mL) and concentrated. The residue was filtrated through silica gel with 10% methanol/dichloromethane and concentrated by rotary evaporation. Purification by radial preparative-layer chromatography (ethyl acetate/hexans 30/70) provided 10-(trimethylsilanylmethoxy)camptothecin (Compound 16) as a yellow solid.

$^1$H NMR (300 MHz, CDCl$_3$) δ 8.24 (s, 1H), 8.10 (d, 1H, J=9.3 Hz), 7.62 (s, 1H), 7.50 (dd, 1H, J$_1$=9.3 Hz, J$_2$=2.4 Hz), 5.75 (d, 1H, J=16.2 Hz), 5.31 (d, 1H, J=16.2 Hz), 5.28 (s, 2H), 3.75 (s, 2H), 3.19 (s, 1H), 2.02-1.85 (m, 2H), 1.05 (t, 3H, J=7.5 Hz), 0.22 (s, 9 H).

MS (m/z, M+1) 451.8

II. Camptothecin Analog Cytotoxicity Experiments in A2780/WT and DX5 Cells

Each of the testing conditions used in this study in both A2780/WT (wild-type) and A2780/DX5 cells were repeated in five to fifteen experiments that were performed on separate days. Each experiment consisted of one microtiter plate with at least eight individual assays of a given drug treatment condition on the plate. The sulforhodamine B (SRB) assay was used to assess cytotoxicity and absorbance at 570 nm (A$_{570}$) in order to calculate the percentage of cell control (or percent cell survival) for the various treatment conditions in the plate wells.

Reagents

Roswell Park Memorial Institute (RPMI 1640) medium, fetal bovine serum (FBS), and L-glutamine were purchased from Gibco BRL. Drugs were dissolved in sterile dimethylsulfoxide (DMSO), from American Type Culture Collection (ATCC) for stock solutions (2.5 to 5.0 mM). Subsequent dilutions were made using cell culture medium (prior to adding the drug to cells). SRB was purchased from Sigma and dissolved in 1.0% acetic acid. Trichloroacetic acid was purchased from VWR International.

Instrumentation

Cells were manipulated in a Class IIA/B3 Biological Safety Cabinet (Forma Scientific) and maintained at 37° C. in a humidified atmosphere containing 5% CO$_2$ in a water-jacketed cell culture incubator (Forma Scientific). Cells were counted using a Coulter-Z1 counter (Beckman-Coulter). Following drug treatment, plates were washed using a Biomek 2000 station (Beckman) and, following exposure to SRB dye, plates were washed using an automated plate washer (Model EL404, Bio-Tek Instruments). Percentage of control was correlated to A$_{570}$ values and determined using a Model EL800 plate reader (Bio-Tek Instruments).

Cell Growth and Viability

Population doubling times for the two cell lines used in this study encompassed a total of five cell doublings corresponding to approximately 5 days for A2780/WT and A2780/DX5 cells. A2780/WT and A2780/DX5 cells were cultured in RPMI 1640 medium supplemented with 10% fetal bovine serum and 1 mM of L-glutamine. Both cell lines were maintained as monolayered cultures in T-25 or T-75 flasks and then seeded to microtiter plate wells for experiments described herein. Prior to SRB assays, cell viability was monitored by evaluation of microtiter plate wells. Dead cells detach and float while living cells remain attached to the bottom of the cell well.

Cytotoxicity Assay (SRB Assay)

The sulforhodamine B (SRB) cytotoxicity assay (see, Skehan P, et al., New colorimetric cytotoxicity assay for anticancer-drug screening. *J. Natl. Cancer Inst.* 82:1107-1112 (1990)) was used to determine the cytotoxic effects of BNP1350, SN-38, topotecan, 9-$NH_2$-CPT, and 9-$NO_2$-CPT on cell growth in vitro. Briefly, after the medium was aspirated from individual plate wells, trichloroacetic acid (100 μL of 10.0% solution) was added to each well, and the plates were incubated at 4° C. for at least 1 hour. The plates were washed five-times with water using an automated microplate washer (Model EL 404, Bio-Tek Instruments), SRB solution (100 μL of 0.4 grams SRB dissolved in 100 mL 1.0% acetic acid) was added, and plates remained at room temperature for 15 minutes. The plates were then washed five-times using acetic acid (1.0 percent), air dried, and bound dye was solubilized in Tris base (150 μL, 10 mM). Plates were agitated (gently) for 5 minutes and the absorbance values of the SRB dye-protein adduct at a 570 nm wavelength ($A_{570}$) were determined using an automated microtiter plate reader equipped with an $A_{570}$ filter (Model EL800, BioTek Instruments).

TABLE VII

Summary of Cytotoxicity Experiments in A2780/WT and DX5 Cells

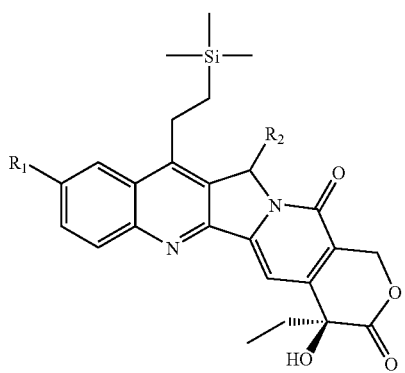

C10-Substituted Karenitecin® Analog

| Compound No. | $R_1$ | $R_2$ | A2780/WT (nM) | A2780/DX5 (nM) | IC50 Ratio |
|---|---|---|---|---|---|
| 1 | —$OCH_3$ | H | 16.8 | 21.9 | 1.3 |
| 2 | $H_3C$—O—$CH_2$—O— | H | 43.4 | 64.8 | 1.5 |
| 3 | HO—$(CH_2)_3$—O— | H | 15.0 | 37.6 | 2.5 |
| 4 | $CH_3O$—$(CH_2)_2$—O— | H | 70.1 | 70.6 | 1.0 |
| 5 | $(CH_3)_2CH$—O— | H | 86.2 | 103.3 | 1.2 |
| 6 | $CH_3CH_2O$— | OH | 158.5 | 167.8 | 1.1 |

TABLE VII-continued

Summary of Cytotoxicity Experiments in A2780/WT and DX5 Cells

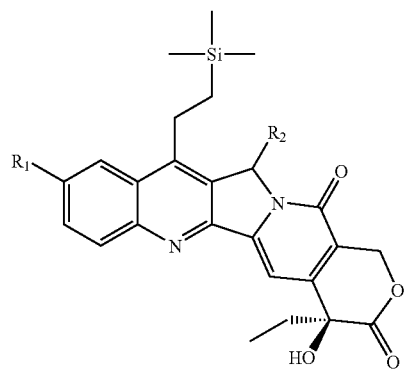

C10-Substituted Karenitecin® Analog

| Compound No. | $R_1$ | $R_2$ | A2780/WT (nM) | A2780/DX5 (nM) | IC50 Ratio |
|---|---|---|---|---|---|
| 7 | $H_2N$-C(O)-$CH_2$-O— | OH | 265.9 | >650 | |
| 8 | $Me_2N$-C(O)-O— | H | 54.8 | 61.1 | 1.1 |
| 9 | EtO-C(O)-$CH_2$-O— | H | 73.9 | 122.8 | 1.7 |
| 10 | $H_2N$-C(O)-$CH_2$-O— | H | 34.1 | 401.1 | 11.8 |
| 12 | morpholine-N-C(O)-O— | H | 65.6 | 134.9 | 2.1 |
| 13 | $Me_2N$-C(S)-O— | H | 116.7 | 228.1 | 2.0 |
| 14 | $CH_3CH_2O$— | H | 14.1 | 17.2 | 1.2 |
| 15 | NC—$CH_2$—O— | H | 9.6 | 18.9 | 2.0 |

It is generally held that an IC50 ratio ≦ 2.0 indicates the potential for high toxicity against tumor cells.

III. Calculation of Free Camptothecin Analogs in Human Plasma

Stocks of various camptothecin analogs were prepared in DMSO. Phosphate buffer was prepared from analytical grade reagents and regenerated cellulose membranes with 12-14 kD molecular weight cut-off (MWCO) were purchased from Spectrum Laboratories. Samples were incubated 48 hours or longer at room temperature until equilibrium was reached. Experiments to determine the percent of free camptothecin/Karenitecin® analogs were performed in triplicate. Optimum HPLC detection conditions for each camptothecin analog were developed using traditional HPLC methods. The results are shown in Table VIII, below.

TABLE VIII

Percent of Free Camptothecin Analogs in Human Plasma (100 nM Compound Concentrations)

| Compound | Percent of Free CPTs |
| --- | --- |
| CPT | 0 |
| Topotecan | 100 |
| CPT-11 | 85 |
| SN-22 | 1 |
| SN-38 | 15 |
| Karenitecin (BNP1350) | 1 |
| 1 (BNP10105) | 3.5 |
| 3 (BNP10107) | 6.8 |
| 4 (BNP10108) | 6 |
| 8 (BNP10112) | 6.4 |
| 10 (BNP10114) | 25 |

From Table VIII, above, it can be concluded that C10-modified Karenitecin® analogs of the present invention possess lower affinity to human plasma proteins, in comparison to SN22, camptothecin (CPT), and even Karenitecin®. Thus, the C10-modified Karenitecin® analogs improve plasma protein binding properties, while concomitantly maintaining the lactone stability and chemotherapeutic potency.

All patents, publications, scientific articles, web sites, and the like, as well as other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicant reserves the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicant reserves the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in the written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The present invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y". The letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and Applicant reserves the right to revise the application or claims to refer specifically to any individual member or any subgroup of members of the Markush group.

What is claimed is:

1. An anti-cancer camptothecin analog selected from the group consisting of: 4-Ethyl-4-hydroxy-9-methoxy-11-(2-trimethylsilanyl-ethyl)-1,12-dihydro-4H-2-oxa-6,12a-diaza-dibenzo[b,h]fluorene-3,13-dione; 7-(2'-Trimethylsilanyl)ethyl-10-(methoxymethyl)oxy camptothecin; 7-(2'-Trimethylsilanyl)ethyl-10-(3'-hydroxypropyl)oxy camptothecin; 7-(2'-Trimethethylsilanyl)ethyl-10-(2'-methoxyethoxy)camptothecin; 7-(2'-Trimethylsilanyl)ethyl-10-isopropoxy camptothecin; 5-Hydroxy-7-(2'-trimethylsilanyl)ethyl-10-ethoxy camptothecin; 5-Hydroxy-7-(2'-trimethylsilanyl)ethyl-10-amidomethoxy camptothecin; 7-(2'-Trimethylsilanyl)ethyl-10-dimethylcarbamic acid camptothecin; 7-(2'-Trimethylsilanyl) ethyl-10-(ethoxycarbonylmethyl)oxy camptothecin; 7-(2'-Trimethylsilanyl)ethyl-10-(amidomethyl)oxy camptothecin; 7-(2'-Trimethylsilanyl)ethyl-10-(carboxymethyl)oxy camptothecin; 7-(2'-Trimethylsilanyl)ethyl-10-(4-morpholinecarbonyl)oxy camptothecin; 7-(2'-Trimethylsilanyl)ethyl-10-(dimethylthiocarbamoyl)oxy camptothecin; 7-(2'-Trimethylsilanyl)ethyl-10-ethoxy camptothecin; 7-(2'-Trimethylsilanyl)ethyl-10-cyanomethoxy camptothecin; 10-(Trimethylsilanylmethyl)oxy camptothecin, and pharmaceutically-acceptable salts thereof.

2. An anti-cancer camptothecin analog having the structural formula:

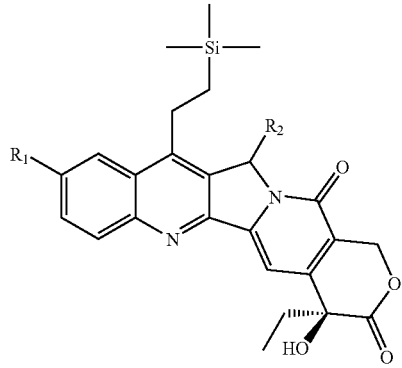

wherein $R_1$ and $R_2$ are selected from the group consisting of: $R_1$ is ethyl-10-methoxy and $R_2$ is hydrogen; $R_1$ is ethyl-10-methoxymethoxy and $R_2$ is hydrogen; $R_1$ is ethyl-10-(3'-hydroxypropoxy) and $R_2$ is hydrogen; $R_1$ is ethyl-10-(2'-methoxyethoxy) and $R_2$ is hydrogen; $R_1$ is ethyl-10-isopropoxy and $R_2$ is hydrogen; $R_1$ is ethyl-10-ethoxy and $R_2$ is hydroxyl; $R_1$ is ethyl-10-amidomethoxy and $R_2$ is hydroxyl; $R_1$ is ethyl-10-(dimethylcarbamoyloxy) and $R_2$ is hydrogen; $R_1$ is ethyl-10-(ethoxycarbonylmethoxy) and $R_2$ is hydrogen; $R_1$ is ethyl-10-(amidomethyloxy) and $R_2$ is hydrogen; $R_1$ is ethyl-10-(carboxymethyloxy) and $R_2$ is hydrogen; $R_1$ is ethyl-10-(4-morpholinecarbonyloxy) and $R_2$ is hydrogen; $R_1$ is ethyl-10-(dimethylthiocarbamoyloxy) and $R_2$ is hydrogen; $R_1$ is ethyl-10-ethoxy and $R_2$ is hydrogen; $R_1$ is ethyl-10-cyanomethoxy and $R_2$ is hydrogen; and pharmaceutically-acceptable salts thereof.

3. The anti-cancer camptothecin analog of claims 1 or 2, wherein the silicon is substituted with germanium.

4. A composition comprising a pharmaceutically-effective amount of an anti-cancer camptothecin analog of any one of claims 1-3 admixed with one or more pharmaceutically-acceptable carriers.

* * * * *